United States Patent
Ito et al.

(10) Patent No.: US 10,448,727 B2
(45) Date of Patent: Oct. 22, 2019

(54) COSMETIC FACIAL MASK

(71) Applicants: JNC CORPORATION, Tokyo (JP); JNC FIBERS CORPORATION, Tokyo (JP)

(72) Inventors: Takafumi Ito, Shiga (JP); Junji Iwata, Shiga (JP); Yasushi Matsuda, Shiga (JP); Mitsuru Kojima, Shiga (JP)

(73) Assignees: JNC CORPORATION, Tokyo (JP); JNC FIBERS CORPORATION, Tokyo (JP)

( * ) Notice: Subject to any disclaimer, the term of this patent is extended or adjusted under 35 U.S.C. 154(b) by 0 days.

(21) Appl. No.: 14/360,308

(22) PCT Filed: Oct. 2, 2012

(86) PCT No.: PCT/JP2012/075496
§ 371 (c)(1),
(2) Date: May 23, 2014

(87) PCT Pub. No.: WO2013/077088
PCT Pub. Date: May 30, 2013

(65) Prior Publication Data
US 2014/0318565 A1 Oct. 30, 2014

(30) Foreign Application Priority Data
Nov. 25, 2011 (JP) ................ 2011-257117
Jul. 9, 2012 (JP) ................ 2012-153604

(51) Int. Cl.
*A45D 44/00* (2006.01)
*A45D 44/22* (2006.01)
*A61F 13/12* (2006.01)

(52) U.S. Cl.
CPC .......... *A45D 44/002* (2013.01); *A45D 44/22* (2013.01); *A61F 13/122* (2013.01)

(58) Field of Classification Search
CPC ..... A45D 44/22; A45D 44/002; A61F 13/122; A61F 2013/00374; A61B 2017/00761
(Continued)

(56) References Cited

U.S. PATENT DOCUMENTS

2008/0069845 A1* 3/2008 Makihara ............. A45D 44/002
424/401
2009/0238849 A1* 9/2009 Iwata ................... A61K 8/0208
424/401
(Continued)

FOREIGN PATENT DOCUMENTS

| CN | 102227181 | 10/2011 |
| JP | 2009-256856 | 11/2009 |
(Continued)

OTHER PUBLICATIONS realself.com, Lower Facelift with Vertical Skin-pull Vectors?. 2009. https://www.realself.com/question/lower-facelift-vertical-vector.*
(Continued)

*Primary Examiner* — Eric J Rosen
*Assistant Examiner* — Mikail A Mannan
(74) *Attorney, Agent, or Firm* — JCIPRNET

(57) ABSTRACT

A cosmetic facial mask is described, having high fitting properties onto skin, an excellent skin tightening effect, and an excellent lift-up effect on a flaccid cheek or face line. The cosmetic facial mask includes a laminate in which a non-elastomeric fiber layer and an elastomer layer are integrated through lamination, and has stretchability in a vertical direction of a face.

8 Claims, 14 Drawing Sheets

(58) Field of Classification Search
USPC .................................................. 606/204.35
See application file for complete search history.

(56) References Cited

U.S. PATENT DOCUMENTS

| 2009/0241242 | A1* | 10/2009 | Beatty | A45D 44/002 |
| | | | | 2/206 |
| 2012/0107387 | A1* | 5/2012 | Ochiai | B32B 5/26 |
| | | | | 424/443 |

FOREIGN PATENT DOCUMENTS

| JP | 2010-281003 | | 12/2010 | |
| WO | 2009/116118 | | 9/2009 | |
| WO | WO2009116118 | * | 9/2009 | ............. A45D 44/12 |
| WO | WO2011004834 | * | 1/2011 | |

OTHER PUBLICATIONS

"The Extended European Search Report", dated Jul. 17, 2015, pp. 1-4.

"International Search Report (Form PCT/ISA/210)", dated Oct. 30, 2012, pp. 1-2.

"Office Action of China Counterpart Application," dated Feb. 14, 2016, with English translation thereof, p. 1-12.

"Office Action of China Counterpart Application" with English translation thereof, dated Sep. 26, 2016, p. 1-9.

"Third Office Action of China Counterpart Application" with English translation thereof, dated Jan. 19, 2017, p. 1-14.

"Office Action of China Counterpart Application," with English translation thereof, dated Aug. 21, 2017, p. 1-10.

"Office Action of Europe Counterpart Application," dated Jul. 14, 2017, p. 1-4.

"Office Action of Korea Counterpart Application," with machine English translation thereof, dated Jul. 17, 2018, p. 1-12.

"Office Action of European Counterpart Application," dated May 3, 2018, p. 1-5.

"Office Action of China Counterpart Application," dated May 24, 2018, with English translation thereof, p. 1-9.

Office Action of China Counterpart Application, with English translation thereof, dated Feb. 15, 2019, pp. 1-19.

"Reexamination Decision of China Counterpart Application," dated Jul. 9, 2019, with English translation thereof, pp. 1-28.

* cited by examiner

COSMETIC FACIAL MASK

CROSS-REFERENCE TO RELATED APPLICATION

This application is a 371 application of the International PCT application serial no. PCT/JP2012/075496, filed on Oct. 2, 2012, which claims priority benefits of Japan Patent Application No. 2011-257117 filed on Nov. 25, 2011, and Japan Patent Application No. 2012-153604 filed on Jul. 9, 2012. The entirety of each of the above-mentioned patent applications is hereby incorporated by reference herein and made a part of this specification.

TECHNICAL FIELD

The invention relates to a cosmetic facial mask to be applied on a face and used, a method for using the same, and a beautifying method using the mask.

BACKGROUND ART

A cosmetic facial mask prepared by impregnating a cosmetic liquid such as a skin lotion, a serum and a milky lotion into a nonwoven fabric has been widely used so far. The mask is one of popular cosmetics items in view of capability of simple use, a high beautification effect and high mental satisfaction of a user as obtained. Expansion is anticipated in the marketplace of the mask in the future.

According to a market research report "Practical use conditions and acceptability search of sheet mask" (Total Planning Center Osaka corp., 2009), 77.5% of women (20 s to 60 s, N=600) being research objects has an experience of using a cosmetic facial mask, and purposes of use thereof were reported to be, from a higher rank, moisturizing (72.5%), skin texture conditioning (35.7%), care of tension and sagging (34.8%), care of a wrinkle and a ripple (29.5%), a make-up sitting improvement purpose (27.7%), a skin-pore tightening purpose (25.6%), and a skin tightening purpose (22.8%) (the rest is omitted). From the contents of the report, consumers in recent years use the cosmetic facial mask not only as a "moisturizing tool" but also as a functional cosmetic material for "tension and sagging," "wrinkle and ripple" and "tightening."

As a mask focusing on the care of tension and sagging and skin tightening, various commercial products and technologies have been developed. For example, as commercially available products, an ear-hooking type mask having ear-hooking holes arranged in both ears parts, and so forth have been long known. Such a mask is a popular commercial product focusing on a lift-up effect on a flaccid cheek, face line or the like, or improvement in a fitting feeling on skin by allowing a cosmetic facial mask to hook on both ears and use in a manner of a hygienic mask. However, the commercial product has had a problem of giving dirty hair during use or giving pain on an ear-hooked site in use.

For a different commercial product, an attempt has also been made on using a raw material having rubber-like stretchability for a mask base material, thereby achieving care of tension and sagging, skin tightening, or improvement in a fitting properties onto skin.

For example, a proposal has been made for a cosmetic facial mask having stretchability in a transverse direction of the face for the purpose of improving the cosmetic facial mask in a degree of fitting onto skin or providing the mask with a lift-up effect on a flaccid cheek or face line (Patent literature No. 1). The mask has realized improvement in the degree of fitting feeling onto skin or provision of the lift-up effect on the flaccid cheek or face line by pinching, with fingers, a face line correction cutting part into a mouth right and left, and pulling up the cutting part in an obliquely upward direction along the face line right and left by applying the jaw as a supporting point.

Moreover, a proposal has also been made for another cosmetic facial mask having features of stretching in the transverse direction of the face, focusing on a fitting feeling onto skin or a skin tightening feeling (Patent literature No. 2, for example). The mask is applied while being elongated in the transverse direction of the face from the mouth to the nose or the cheek, thereby improving fitting onto the skin or providing the skin with a skin tightening effect.

CITATION LIST

Patent Literature

Patent literature No. 1: WO 2009/116118 A.
Patent literature No. 2: JP 2010-281003 A

SUMMARY OF INVENTION

Technical Problem

However, the conventional masks have a problem in which the skin on the cheek part and the jaw part as lifted up in the direction of both ears is gradually returned to a lower position as caused by original stretchability of the base material. Therefore, the masks are still far from satisfactory. For example, no sufficient lift-up feeling is obtained, or a lift-up effect on a flaccid cheek or face line as desired by many women is quite difficult to sufficiently achieve.

Consequently, in view of such a problem, an object of the invention is to provide a cosmetic facial mask having high fitting properties onto skin, an excellent effect on skin tightening, and an excellent lift-up effect on a flaccid cheek or face line.

Solution to Problem

The inventors have diligently continued to conduct research in order to solve the problem. As a result, the inventors have found that the problem can be solved by using a cosmetic facial mask comprising a laminate in which a non-elastomeric fiber layer and an elastomer layer are integrated through lamination, and having stretchability in a vertical direction of the face, and have completed the invention based on the finding.

The invention has constitutions described below.

Item 1 is a cosmetic facial mask comprising a laminate in which a non-elastomeric fiber layer and an elastomer layer are integrated through lamination, and having stretchability in a vertical direction of the face.

Item 2 is the cosmetic facial mask according to item 1 of which a stress at 50% elongation in a wet state is in the range of 0.4 to 5.0 N/25 mm, and an elongation recovery ratio at 50% elongation in the wet state is 50% or more.

Item 3 is the cosmetic facial mask according to item 1 or 2 of which a stress at 25% elongation recovery in a wet state is in the range of 0.02 to 1.5 N/25 mm.

Item 4 is the cosmetic facial mask according to any one of items 1 to 3 in which the non-elastomeric fiber layer includes a fiber layer obtained by aligning fibers in one direction by carding, and the direction of aligning the fibers is made coincide with a cross direction of the cosmetic facial mask.

Item 5 is the cosmetic facial mask according to any one of items 1 to 4 in which the non-elastomeric fiber layer is subjected to nonwoven fabric formation by entangling fibers with each other in a fiber layer in the thickness direction of the fiber layer.

Item 6 is the cosmetic facial mask according to any one of items 1 to 5 in which the elastomer layer is a nonwoven fabric formed by at least one kind of method selected from the group of a melt-blown method and a spunbond method.

Item 7 is a method for using a cosmetic facial mask according to any one of items 1 to 6, wherein the cosmetic facial mask is worn while being stretched in a downward direction and/or a right-left diagonally downward direction of the face by applying as a supporting point arbitrary one or more points of a temple part, a cheek part and a lower part of nose.

Item 8 is a beautifying method using the cosmetic facial mask according to any one of items 1 to 6.

Advantageous Effects of Invention

The cosmetic facial mask of the invention has moderate stretchability in a vertical direction of the face, and therefore has a satisfactory wearing feeling, fitting feeling or tightening feeling onto the face, and also an excellent lift-up effect on a site such as a jaw part, a mouth part, a cheek part and an eye part.

DESCRIPTION OF EMBODIMENTS

Figure 1:
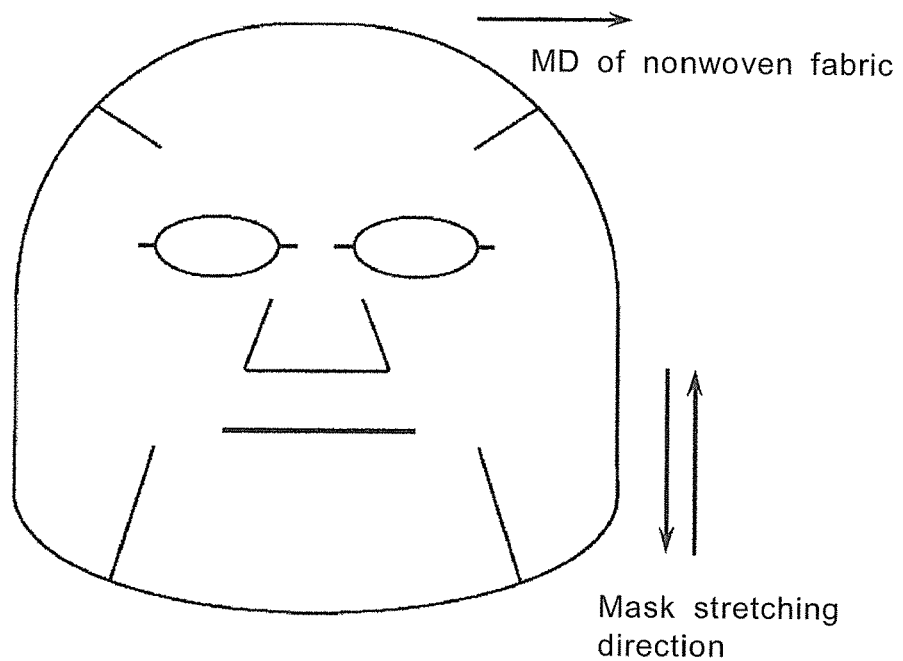
FIG. 1 is a schematic constitutional diagram showing a cosmetic facial mask according to one embodiment of the invention.

The invention is described in details below according to embodiments.

A cosmetic facial mask of the invention comprises a laminate in which a non-elastomeric fiber layer and an elastomer layer are integrated through lamination, and has stretchability in a vertical direction of a face on which the mask is worn.

"Having stretchability in a vertical direction of a face" herein means that the cosmetic facial mask has stretchability in a direction vertical to the face on which the cosmetic facial mask is worn.

Non-Elastomeric Fiber Layer

In the invention, the non-elastomeric fiber layer means a fiber layer constituted using a non-elastomer raw material, and having elongatability at least in one direction. More specifically, the non-elastomeric fiber layer means a fiber layer having non-elastomeric properties and elongatability at least in one direction, in other words, a fiber layer having no elastomeric properties (rubber-like elasticity), but having elongatability at least in one direction. Specifically, the non-elastomeric fiber layer includes a fiber layer having elongatability but having a low recovery ratio after elongation, and preferably, a fiber layer in which the "elongation recovery ratio at 50% elongation in a wet state" measured under conditions as described later is less than 50%, preferably 35% or less. Such a non-elastomeric fiber layer is integrated through lamination with an elastomer layer, thereby moderate stretchability and a moderate stress during elongation being provided for the resulting cosmetic facial mask.

The non-elastomeric fiber layer is constituted using the non-elastomer raw material. The non-elastomer raw material is ordinarily used in the form of fibers to constitute the fiber layer. Therefore, if the non-elastomer raw material is natural fibers, the material can be utilized without forming fibers, but if the non-elastomer raw material is a raw material resin such as a thermoplastic resin, the material can be utilized after the material is formed into fibers. As the non-elastomeric fiber layer, paper, a nonwoven fabric, a woven fabric and so forth can be preferably utilized. In view easy handling and good texture when the layer is used in the form of a cosmetic facial mask, and also excellent cost performance, the non-elastomeric fiber layer is further preferably used in the form of a nonwoven fabric. As the fibers constituting the non-elastomeric fiber layer, for example, natural fibers such as pulp, cotton, linen, bamboo, kenaf, silk and wool, regenerated fibers such as viscose rayon, cupra and lyocell, or synthetic fibers such as polyethylene fibers, polypropylene fibers, polyethylene terephthalate fibers, polybutyrene terephthalate fibers, nylon fibers and polyacrylic fibers can be used. Two or more kinds of fibers may be mixed and used. For example, a fiber blend of viscose rayon fibers with pulp, a fiber blend of viscose rayon fibers with cotton, a fiber blend of viscose rayon fibers with polyethylene terephthalate fibers, and a fiber blend of cotton with polyethylene terephthalate fibers can be utilized. Moreover, fibers obtained by mixing two or more kinds of non-elastomer raw materials may be used. As the non-elastomer raw material, a thermoplastic resin such as crystalline polyethylene, crystalline polypropylene, polyethylene terephthalate, polybutyrene terephthalate, nylon and polyacrylonitrile can be utilized. Fibers may be produced by mixing two or more kinds thereof.

The non-elastomeric fiber layer is preferably excellent in hydrophilicity and liquid retention properties. The fiber layer is preferably constituted of hydrophilic fibers obtained using a hydrophilic raw material, and from the non-elastomer raw material or the fibers formed therefrom as exemplified above, materials generally evaluated to have hydrophilicity can be selected and used. In view of hydrophilicity, a raw material (cellulosic raw material) mainly formed of cellulose such as cotton, linen, rayon, cupra and pulp is preferred. A nonwoven fabric containing one kind or more kinds of the raw materials is excellent in hydrophilicity, water-absorbing properties and liquid retention properties, and can be preferably used in the form of a cosmetic facial mask.

The fibers constituting the non-elastomeric fiber layer may be short fibers or long fibers. In the invention, the short fibers mean fibers having a fiber length of 0.5 to 100 mm, and the long fibers mean fibers having a fiber length exceeding 100 mm, and include continuous fibers.

Specific examples of the non-elastomeric fiber layer include a fiber layer (card web) formed by aligning short fibers in one direction by carding, an air-laid web formed by stacking short fibers at random, or a wet paper-making web. If a wet paper-making web is used as the non-elastomeric fiber layer, the resulting cosmetic facial mask shows a good wearing feeling or good wearing stability. In view of more easily obtaining the fiber layer having elongatability at least in one direction, the non-elastomeric fiber layer preferably includes a fiber layer formed by aligning short fibers in one direction by carding.

The non-elastomeric fiber layer is preferably formed into a nonwoven fabric by entangling the fibers with each other in the fiber layer in the thickness direction of the fiber layer. As a raw material of the non-elastomeric fiber layer, when short fibers are used, such nonwoven fabric formation can be suitably achieved by a needle punch method, a water stream entangling method or the like. A nonwoven fabric obtained by the water stream entangling method is preferred in view of the wearing feeling or wearing stability of the cosmetic facial mask.

In particular, the nonwoven fabric according to the water stream entangling method, as obtained by performing water stream entangling processing to a card web formed by aligning short fibers in one direction to allow three-dimensional entanglement of the short fibers, has good elongatability in a direction (CD of the nonwoven fabric) perpendicular to the direction of the fibers aligned in one direction, and therefore such a nonwoven fabric is preferred.

The fiber diameter of the fibers constituting the non-elastomeric fiber layer is not particularly limited, but is preferably 0.1 to 100 μm, and more preferably 4 to 50 μm.

In view of desired strength, retention for a cosmetic liquid, appearance, concealability, a volume feeling during use, and elongatability in a wet state in the form of a cosmetic facial mask, the basis weight of the non-elastomeric fiber layer is preferably 5 to 150 g/m$^2$, and more preferably 10 to 100 g/m$^2$.

To the non-elastomeric fiber layer of the invention, various modifiers such as a stabilizer, an antibacterial agent, a coloring agent, a lubricant, a hydrophilic agent, an antistatic agent, a charging agent, a slipping agent and an antiblocking agent, or an elastomer raw material such as a thermoplastic elastomer, may be added within a range in which the advantageous effects of the invention are not adversely affected.

Elastomer Layer

The elastomer layer of the invention may include a layer structurally exhibiting elastomeric properties as derived from a fiber form or a layer constitution, or a layer produced using an elastomer raw material having elastomeric properties in a raw material itself. In order to secure desired stretchability, fitting capability, a skin tightening effect or a lift-up effect in the form of a cosmetic facial mask, the elastomer layer of the invention is preferably 50% or more in the "elongation recovery ratio at 50% elongation in a wet state" as described later, and more preferably 65% or more.

The elastomer layer of the invention can be used in a film shape, a sheet form, a net shape, a nonwoven fabric shape, a woven fabric shape or the like, as long as the layer has elastomeric properties as described above. In view of easy handling, texture softness, air permeability and liquid permeability when the layer is used in the form of a cosmetic facial mask, and also excellent cost performance, the nonwoven fabric shape is preferred.

The layer structurally exhibiting elastomeric properties as derived from a fiber form or a layer constitution is not particularly limited, and specific examples include a web containing short fibers provided with solid crimps, and a nonwoven fabric obtained by three-dimensionally entangling the fibers by a needle punch method, a water stream entangling method or a high-pressure steam entangling method, and also a woven fabric provided with stretchability by a processing method such as a stockinet stitch, a garter stitch and a rib stitch. Moreover, the layer may include a layer provided with stretchability by drawing processing using at least a pair of rolls in which tooth grooves are engaged. Moreover, the layer may be a layer including, in at least one layer, a nonwoven fabric prepared by using a web containing potentially crimpable fibers and heating the web to develop crimps of fibers and thereby entangle the fibers to unify the web.

When the elastomer layer of the invention includes a layer produced using an elastomer raw material having elastomeric properties in the raw material itself, specific examples of the elastomer raw materials to be used include various kinds of rubber such as natural rubber, chloroprene rubber, nitrile rubber, ethylene-propylene rubber, urethane rubber and silicone rubber, and thermoplastic elastomers such as a styrene-based elastomer, an olefin-based elastomer, a polyurethane-based elastomer, a polyester-based elastomer, a polyamide-based elastomer and a vinyl chloride-based elastomer. In view of the fitting feeling associated with flexibility or stretchability of the cosmetic facial mask impregnated with a cosmetic liquid, or the like, a styrene-based elastomer, an olefin-based elastomer or a urethane-based elastomer is preferred.

In order to appropriately adjust performance such as the stretchability in the elastomer layer, two or more kinds of different fibers selected from the above elastomer raw materials may be mixed in the elastomer layer.

The fibers constituting the elastomer layer may be short fibers or long fibers.

As the elastomer layer of the invention, a nonwoven fabric formed of long fibers as produced by a spunbond method or a melt-blown method using the thermoplastic elastomer raw material is preferred in view of air permeability, liquid permeability, stretchability, and also cost performance. In particular, the melt-blown method is preferred not only because ultrafine fibers are obtained but also because the thermoplastic elastomers can be efficiently formed into a nonwoven fabric without a fear of spinning breakage. Moreover, the elastomer layer may be produced in combination of the spunbond method and the melt-blown method. Specifically, the elastomer layer can be produced by integrating, through lamination, a nonwoven fabric obtained by the spunbond method and a nonwoven fabric obtained by the melt-blown method.

The fiber diameter of fibers constituting the elastomer layer is not particularly limited, but is preferably in the range of 15 μm or less, and further preferably, in the range of 10 μm or less in order for the cosmetic facial mask to have desired flexibility and fitting capability onto the skin.

The basis weight of the elastomer layer is not particularly limited, but is preferably in the range of 10 to 200 g/m², and more preferably in the range of 15 to 150 g/m², in order to secure desired stretchability, tightening effect and lift-up effect in the form of a cosmetic facial mask.

In the elastomer layer of the invention, various modifiers such as a hydrophilic agent, a lipophilic agent, a slipping agent and an antiblocking agent, or a non-elastomeric raw material such as polyethylene, polypropylene, polystyrene, polyethylene terephthalate and nylon, may be added as a modifier or an extending agent within the range in which the advantageous effects of the invention are not adversely affected.

Integration Through Lamination

The cosmetic facial mask of the invention is constituted by integrating a non-elastomeric fiber layer and an elastomer layer through lamination, and forming the resulting laminate into a shape of an objective cosmetic facial mask. Specific examples of the laminates include: a laminate prepared by bonding, using an adhesive or a binder material, a non-elastomeric fiber layer and an elastomer layer as separately produced, a laminate prepared by laminating an elastomer layer with a non-elastomeric fiber layer, a laminate prepared by performing thermocompression bonding of an elastomer layer with a non-elastomeric fiber layer using an embossing roll or a calendering roll, and a laminate prepared by entangling an elastomer layer with a non-elastomeric fiber layer by a water stream entangling method or a high-pressure steam entangling method.

A laminate prepared by laminating a non-elastomeric fiber layer with an elastomer layer and then performing partial thermocompression bonding using an embossing roll is preferred, because delamination resistance to a stretching stress applied upon using the laminate in the form of the cosmetic facial mask is increased.

The conditions of partial thermocompression bonding using the embossing roll are not particularly limited, as long as the bonding is performed under conditions in which interlayer strength and texture of the laminate are maintained, but the embossing area ratio is preferably in the range of 3 to 40%, and more preferably in the range of 4 to 30%.

Specific examples of the laminate obtained by performing partial thermocompression bonding using the embossing roll include a laminate prepared by performing water stream entangling processing to a card web obtained by aligning short fibers containing cellulosic fibers in one direction by carding, using as a non-elastomeric fiber layer a nonwoven fabric according to a water stream entangling method as obtained by 3D-entangling the short fibers, using an elastomer raw material to form a nonwoven fabric as an elastomer layer by a spunbond method or a melt-blown method, laminating the non-elastomeric fiber layer and the elastomer layer, and then performing partial thermocompression bonding using an embossing roll. The resulting laminate is preferred in view of good liquid permeability, air permeability, softness of texture or delamination resistance as required for the cosmetic facial mask, and also satisfactory cost performance.

In order for the laminate made through lamination integration of the non-elastomeric fiber layer and the elastomer layer to have desired flexibility, fitting feeling, tightening effect or lift-up effect in the form of the cosmetic facial mask of the invention, the stress at 50% elongation in a wet state as measured under conditions as described later is preferably in the range of 0.4 to 5.0 N/25 mm, and the elongation recovery ratio at 50% elongation is preferably in the range of 50% or more. The stress at 50% elongation in a wet state is more preferably in the range of 0.5 to 2.5 N/25 mm, and the elongation recovery ratio at 50% elongation is more preferably in the range of 60% or more. As described later, the "elongation recovery ratio at 50% elongation" is also expressed in terms of a value measured using a test specimen in the wet state as in the case of the "stress at 50% elongation."

Moreover, a laminate satisfying the requirements described above and having a stress at 25% elongation recovery in a wet state as measured under conditions as described later in the range of 0.02 to 1.5 N/25 mm, or a laminate more preferably having a stress at 25% elongation recovery in a wet state in the range of 0.1 to 0.9 N/25 mm shows a particularly excellent tightening effect and lift-up effect, and thus can be suitably used for the cosmetic facial mask of the invention.

The basis weight of the laminate in which the non-elastomeric fiber layer and the elastomer layer are integrated through lamination is not particularly limited, but is preferably in the range of 10 to 200 g/m$^2$, and more preferably in the range of 15 to 150 g/m$^2$, in view of provision of liquid retention capability and a volume feeling during use as required in the form of the cosmetic facial mask.

The thickness of the laminate is not particularly limited, but the thickness upon applying a load of 2 kgf/cm$^2$ (0.196 MPa) is preferably in the range of 0.2 to 0.7 mm in view of impregnation property and permeability of the cosmetic liquid.

To the laminate to be used in the invention, drawing processing may be applied using at least a pair of rolls with which the tooth grooves are engaged in order to physically further provide the laminate itself with stretchability or flexibility. The drawing processing may be applied in the MD, the CD or both directions of the laminate.

Cosmetic Facial Mask

The cosmetic facial mask of the invention is manufactured using the laminate in which the non-elastomeric fiber layer and the elastomer layer are integrated through lamination. Specifically, the mask is obtained by cutting out, from the laminate, a desired shape in a manner such that the direction of the laminated non-elastomeric fiber layer having elongatability, i.e., the direction of the laminate having stretchability, coincides with the vertical direction of face in the cosmetic facial mask.

When the non-elastomeric fiber layer includes a fiber layer obtained by aligning fibers in one direction by carding, the cosmetic facial mask may be cut out in a manner such that the alignment of the fibers coincides with the cross direction of the cosmetic facial mask, i.e., the transverse direction of the face perpendicular to the vertical direction of the face.

The cosmetic facial mask of the invention is cut out into a shape suitable for covering the face, and processed. In the cosmetic facial mask, punched parts or cut parts are arranged, when necessary, for example, in parts corresponding to the eyes, the nose and the mouth. The processing method is not particularly limited, but punching using a Thompson blade or use of a rotary die cutter is preferred.

The cosmetic facial mask cut out from the laminate has characteristics derived from the laminate, more specifically, a suitable stress at 50% elongation in the wet state, a suitable elongation recovery ratio at 50% elongation in the wet state, a suitable stress at 25% elongation recovery in the wet state, and a suitable basis weight, thickness or the like.

The thus obtained cosmetic facial mask of the invention has moderate stretchability and moderate elongation stress in the vertical direction of the face, and therefore can exhibit a sufficient lift-up effect on a flaccid cheek and a face line, none of which is exhibited by a conventional cosmetic facial mask.

The cosmetic facial mask may be appropriately cut out into various shapes depending on the purpose, and the shape is not particularly limited. For example, the mask may be of a one-piece type for wholly covering a face using one sheet, a separate type for wholly covering the face in combination of two or more sheets, or may have a shape of lengthening the neckline to cover a neck portion. Furthermore, the mask may have a shape for covering only a part of the face (the eyes, month, nose or cheek, for example). Moreover, the scope of the invention also includes a face mask having a constitution in which a member having stretchability in the vertical direction of the face is constituted to cover a part a lift-up effect of which is desirably enhanced and a member having stretchability or elongatability in a direction and/or strength different from that of the above stretchability, or having neither elongatability nor stretchability covers other parts of the face.

In the cosmetic facial mask of the invention, a good wearing feeling is obtained even without particularly making a cut, but for the purpose of more satisfactorily fitting the mask to the face to improve the tightening effect or the lift-up effect, or the like, arbitrary number and arbitrary depth of cuts may be made in arbitrary position and direction of the cosmetic facial mask according to the shape of the cosmetic facial mask. As a noteworthy feature of the cosmetic facial mask of the invention, when the number and positions of cuts in a jaw part are adjusted, a cosmetic facial mask having a particularly strong jaw part lift-up feeling, a cosmetic facial mask having a particularly strong cheek part lift-up feeling, a cosmetic facial mask having a strong tightening feeling of a lower part of face as a whole while the jaw part lift-up feeling is somewhat poor, or the like can be obtained, thereby allowing wide and appropriate use of the mask in a different manner according to a product concept.

Although not being particularly limited, for example, a cosmetic facial mask of the invention constituted in the embodiment of Example 1 described later may be prepared by arranging a cut from both right-left jaw parts toward the end direction of the month so that the jaw part lift-up feeling becomes particularly strong. Moreover, in a cosmetic facial mask of the embodiment of Example 2 described later as prepared by arranging a cut from the jaw part center toward the month center, the cheek part lift-up feeling becomes particularly strong. Moreover, in a cosmetic facial mask of an embodiment of Example 3 described later as prepared without arranging a cut in the jaw part, the jaw part lift-up feeling is somewhat poor, but the tightening feeling of a lower part of face as a whole becomes strong.

Furthermore, in a cosmetic facial mask of the invention, any other raw material may be laminated (integrated through lamination) with at least part of the cosmetic facial mask within the range in which advantageous effects of the invention are not adversely affected. Although a site at which the lamination is made or any other raw material used for lamination is not particularly limited, a film, a woven fabric, a nonwoven fabric or the like is preferred, and by selecting from a non-stretchable raw material, a stretchable raw material, a hydrophilic raw material, a non-hydrophilic raw material for a site at which efficacy is desirably locally obtained or the like depending on the use and the purpose, thereby allowing partial control of stretchability, partial control of liquid retention capability or partial provision of warmth retaining capability.

In the cosmetic facial mask, the cosmetic liquid may be contained beforehand, immediately before use or during use. Moreover, it is possible to use a mask containing no cosmetic liquid as a wrap material after the cosmetic liquid is applied onto the face.

In the invention, the "cosmetic liquid" includes a gel-like cosmetic ingredient. As is clear from using "ELIXIR SUPERIER Lift Moist Lotion III" (trade name) made by Shiseido Co., Ltd., specifically, as a cosmetic liquid in Examples described later, "in the invention, "cosmetic liquid" contains a gel-like cosmetic ingredient" means that "in the invention, "cosmetic liquid" may be literally a liquid cosmetic ingredient, or alternatively a gel-like cosmetic ingredient."

A mask prepared by coating a hydrous gel onto the cosmetic facial mask according to the invention is also included in the scope of the cosmetic facial mask of the invention. The hydrous gel is not particularly limited, and specific examples thereof include agarose gel, sodium polyacrylate gel, bacterial cellulose gel and gelatin gel, etc. In the cosmetic facial mask prepared by coating a hydrous gel, the cosmetic liquid may be also contained beforehand, immediately before use or during use. Moreover, it is possible to use a mask that is prepared by coating a hydrous gel and contains no cosmetic liquid as a wrap material after the cosmetic liquid is applied onto the face. Furthermore, it is possible that the cosmetic ingredient described later is added to hydrous gel and then the resulting material is coated onto the cosmetic facial mask of the invention.

The cosmetic liquid to be used is not particularly limited, and a commercially available cosmetic liquid or the like can be used. Nevertheless, the cosmetic liquid preferably contains a cosmetic ingredient such as a moisturizing ingredient, an emollient ingredient, a blood circulation acceleration ingredient, a cleansing ingredient, an antiperspirant ingredient, a fragrant ingredient, a whitening ingredient, a slimming ingredient, an antimicrobial ingredient and an ultraviolet rays protective ingredient.

The content of the cosmetic liquid in the cosmetic facial mask is not particularly limited, as long as it is within the range in which no dripping is caused and efficacy is effectively developed. In general, the cosmetic liquid can be impregnated in the range of 100 to 2000 parts by mass, and preferably 500 to 1500 parts by mass, based on 100 parts by mass of the cosmetic facial mask.

When the nonwoven fabric water according to the water stream entangling method, which is obtained by performing water stream entangling processing to a card web in which short fibers are aligned in one direction in the non-elastomeric fiber layer to allow three-dimensional entangling, is used in the cosmetic facial mask of the invention, the one direction (MD of the non-woven fabric) in which the fibers are aligned is arranged so as to coincide with the face transverse direction. Therefore, in comparison with a conventional mask having stretchability in the face transverse direction (the one direction (MD of the nonwoven fabric) in which the fibers are arranged is arranged so as to coincide with the face vertical direction), the cosmetic facial mask has a feature of scarce occurrence of a capillary phenomenon in the mask downward direction and scarce occurrence of dripping during wearing. Moreover, in particular, the cosmetic facial mask is effective in suppressing dripping of the cosmetic liquid to the eyes or the mouth in a cut part or a punched part that is arranged toward the cross direction of the face mask at the site corresponding to the eyes or the mouth of the cosmetic facial mask. The cosmetic facial mask of the invention is suitable also for a life style of women who move her body in housekeeping or the like while keeping wearing of the cosmetic facial mask.

In the cosmetic facial mask of the invention, the non-elastomeric fiber layer and the elastomer layer may each independently be present in a plurality of layers, within the range in which the advantageous effects of the invention are not adversely affected.

Method for Using Cosmetic Facial Mask and Beauty Regimen

As described above, there are a large number of cosmetic facial masks focusing on the lift-up effect on the flaccid cheek or face line. With reference to an article of a monthly "MISS" 2011 November (Sekai Bunka Publishing Co., Ltd.), or the like, commercially available cosmetic facial masks focusing on the effect have been investigated. As a result, the masks focusing on the effect are merely masks that are worn in a manner of being lifted in an oblique upward direction (ear direction) applying the jaw as a supporting point, without regard to the ear-hooking type mask or the mask having stretchability in the face transverse direction. Moreover, a mask boastfully stating "stretch" merely includes a commercial product having a design of extending in the face transverse direction. The results are estimated to be caused by consumer's recognition that "the lift-up mask should be worn along the face line to be used in a manner of being lifted up in the oblique upward to upward directions by applying the jaw as a supporting point." Therefore, for the cosmetic facial mask using a stretchable raw material, in order to satisfy the consumer's attitude as described above, a design of stretching in the face transverse direction is thought to be widely and generally adopted, in which the mask is easily lifted up in the ear direction, and a fitting feeling to the face line is obtained when the mask is elongated.

In contrast, the cosmetic facial mask of the invention has a feature of having stretchability in the direction vertical to the face, and is borne from an idea completely different from a conventional mask that stretches in the face transverse direction. Specifically, upon wearing the cosmetic facial mask of the invention to the face, the mask is used while being elongated in a downward direction, and not in the face upward direction. Thus, a contractive force toward the face upward direction is generated in the laminate constituting the mask, thereby allowing all sites women particularly desire lift-up, which include the jaw part, the mouth part, the cheek part, the eye part and so forth, to be lifted up in the desired direction. As a result, the cosmetic facial mask is effective in providing a wearer with an efficient lift-up feeling and fitting feeling.

The cosmetic facial mask of the invention is worn on the face. For the purpose of exhibiting the lift-up effect of the cosmetic facial mask of the invention, and simultaneously caring skin by a moisturizing ingredient or the like, the cosmetic facial mask is preferably used while containing a cosmetic liquid, but is not particularly limited thereto. It is also possible to use a mask containing no cosmetic liquid as a wrap material after the cosmetic liquid is applied onto the face. The method for containing the cosmetic liquid in the cosmetic facial mask and the timing of the containment are not particularly limited. The cosmetic liquid may be contained in the cosmetic facial mask before or after wearing the cosmetic facial mask on skin.

The method for wearing (or using) the cosmetic facial mask onto the face is not particularly limited.

In order to obtain a high lift-up effect, the mask is preferably worn by applying as the supporting point arbitrary one or more points of the temple part, the cheek part and the lower part of nose while being stretched in a downward direction and/or a right-left diagonally downward direction of the face. For example, when lift-up of the jaw part to the mouth part is desired, while holding the mask using the thumb and the index finger of the right hand or the left hand such that the lower part of nose to the cheek central part (the vicinity a little upper than the mouth part) serves as a supporting point, a mask lower surface part is stretched in the downward direction and/or the right-left diagonally downward direction of the face from the supporting point to fit and fix the mask lower end to the jaw lower part, a desired effect can be efficiently obtained. When lift-up of the jaw part to the cheek part is desired, a similar operation may be performed just by applying the lower part of nose to the cheek upper part (vicinity of the eye part) as a supporting point. When lift-up of the jaw part to the eye part is desired, a similar operation may be performed just by applying the temple part as the supporting point. Moreover, after the mask is worn by any one of the procedures, stretching is finely adjusted while the supporting point part is sequentially shifted, thereby allowing an adjustment of intensively lifting up a desired place such as the eye part, the cheek part, the mouth part and the jaw part. Furthermore, the mask has repeated stretchability, and therefore even when the mask has shifted during wearing or erroneous wearing has been made, by performing a similar procedure again, an effect of providing the wearer with the lift-up feeling and the fitting feeling is obtained, and thus the mask is excellent also in the above point.

The cosmetic facial mask of the invention demonstrates an excellent lift-up effect on all sites women particularly desire lift-up, such as the jaw part, the mouth part, the cheek part and the eye part. Further, the cosmetic facial mask of the invention has moderate stretchability and stress at elongation, and in combination therewith, a member of the mask has inherently good lift-up ability. Therefore, the mask has no need of exhibiting the lift-up ability by adopting the form of an ear-hooking type or the like, and thus is not accompanied by unpleasant pain in the ear part or the like. Moreover, the cosmetic facial mask of the invention is excellent also in the fitting feeling onto skin, and can also be simply used. More specifically, the mask is reasonably a tool for proposing a new beautifying method to contemporary women who are busy in working, housekeeping, child-raising or the like and have high sense of beauty.

The beautifying method of the invention is not particularly limited, as long as the method utilizes the stretchability of the cosmetic facial mask in the vertical direction according to the invention. Specific examples thereof include a massage method, a pressure point stimulation method and a wrinkle improvement method in which the mask of the invention is used. Specifically, an advanced operation such as preparation to sharp face lines by facial massage has been difficult for general consumers having no expertise to carryout at home. However, if the cosmetic facial mask of the invention is used, uniform pressure can be continuously applied in the upward direction of each site of the face as in an operation by a cosmetics expert in an aesthetic salon or the like, thereby allowing obtaining of an effective massage effect, a small face effect or the like simply and in a short period of time even in a general household. Moreover, as described above, in the cosmetic facial mask of the invention, a supporting point position during wearing is changed, or a mask cut position is adjusted, thereby allowing lift-up of an arbitrary position of the face. If the function is used, "pressure point stimulation" can be performed as in finger pressure. Further, the cosmetic facial mask of the invention tightly fits to the face by vertical stretching, and therefore an active ingredient of the cosmetic liquid contained in the mask can be uniformly spread to the whole skin. Therefore, if the cosmetic facial mask of the invention is continuously used, an effect on improving skin texture and dry wrinkle are expected to be obtained.

The cosmetic facial mask of the invention may be used by bringing either the non-elastomeric fiber layer or the elastomer layer into contact on the skin side, but preferably by placing on the skin side the elastomer layer having soft texture and showing high fitting properties onto skin.

EXAMPLES

Details of the invention are described below by way of Examples. However, the present Examples in no way limit the invention. In Examples, for a laminate formed by lamination integration of a non-elastomeric fiber layer with an elastomer layer, ELFino (registered trademark) LM6020-38 being a nonwoven fabric made by JNC Corporation was used.

Moreover, in Comparative Examples, two kinds of commercially available nonwoven fabrics for cosmetic masks were used. Between the nonwoven fabrics, nonwoven fabric 2 was a card nonwoven fabric obtained by entangling, by a water stream entangling method, fibers of a card web in which viscose-rayon short fibers and single fibers of synthetic fibers were mixed, and nonwoven fabric 3 was a wet long-fiber nonwoven fabric obtained by entangling, by a water stream entangling method, fibers of a cupra long-fiber fleece.

In addition, the material names and the numerical values (%) as described in the column of "non-elastomeric fiber layer" in Table 1 show the proportion by mass (%) of the contained fibers composed of the materials. More specifically, a description of a plurality of materials means that fibers obtained using the materials are mixed at respective proportions by mass (%).

The basis weight, the stress at 50% elongation in a wet state, and the elongation recovery ratio at 50% elongation of each nonwoven fabric were measured by the methods described below.

Basis Weight of Nonwoven Fabric

Measurement was carried out in accordance with JIS L1906 "Test Methods for Non-Woven Fabrics made of Filament Yarn." Test specimens each having a size of 20 cm×20 cm were cut out from five arbitrary places of each nonwoven fabric described in Table 1, and then the weight of each test specimen was measured using an electronic balance, and a mean value was converted into a mass per $m^2$ to be taken as the basis weight of the nonwoven fabric.

Stress at 50% Elongation in Wet State

Test specimens each having a size of 25 mm width and 150 mm length were cut out from the elastomer layer, the non-elastomeric fiber layer and the laminate thereof under conditions described below, respectively.

In the case of the elastomer layer, a test specimen was cut out such that the stretching direction thereof coincided with the longitudinal direction thereof. In the case of the non-elastomeric fiber layer or the laminate of the non-elastomeric fiber layer and the elastomer layer, a test specimen was cut out such that the length direction thereof coincided with the direction in which the non-elastomeric fiber layer had elongatability. Moreover, in particular, a test specimen is cut out such that the length direction thereof coincided with the direction (CD direction) perpendicular to the one direction in which fibers constituting the non-elastomeric fiber layer were aligned.

Subsequently, the test specimens were immersed into purified water at room temperature (25° C.) for 10 minutes to uniformly impregnate purified water thereinto, thereby preparing each test specimen in a wet state. The thus obtained test specimen was elongated, using an autograph AG-500D model (made by Shimadzu Corporation), in accordance with JIS L1906 "Test Methods for Woven Fabrics," to a chuck distance of 150 mm under conditions of a chuck interval of 100 mm and a rate of testing stress of 300 mm/minute, to measure a stress at the point.

Elongation Recovery Ratio at 50% Elongation in Wet State

A test material was elongated to a chuck interval of 150 mm under conditions identical with the conditions for the stress at 50% elongation described above. Subsequently, a point elongated to 150 mm was applied as a starting point, and the test material was returned at an identical rate to measure length L (mm) at which a residual stress became 0 as obtained from a load-elongation curve, thereby determining an elongation recovery ratio according to the numerical expression described below. "Under conditions identical with the conditions for the stress at 50% elongation described above" herein obviously means measurement of the elongation recovery ratio after the test specimen was adjusted in the wet state in a manner similar to the measurement of the stress. More specifically, "elongation recovery ratio at 50% elongation" referred to herein means "elongation recovery ratio at 50% elongation in the wet state."

$$\text{Elongation recovery ratio at 50\% elongation} = \{(50^{*1}-L)/50^{*1}\} \times 100$$

$*1$: Length (50 mm) at which the test specimen was elongated.

Stress at 25% Elongation Recovery in Wet State

A test material was elongated to a chuck interval of 150 mm under conditions identical with the conditions for stress at 50% elongation described above, and subsequently returned to a chuck interval of 125 mm at an identical rate to measure a stress at the point.

Table 1 shows the material, the basis weight, the stress at 50% elongation in a wet state, the elongation recovery ratio at 50% elongation in a wet state, and the stress at 25% elongation recovery in a wet state of nonwoven fabric 1 (laminate), nonwoven fabric 2 or nonwoven fabric 3 used in Examples and Comparative Examples.

Preparation 1 of Cosmetic Facial Mask (Example 1, Comparative Examples 1 and 2)

Each nonwoven fabric shown in Table 1 was adjusted in the direction of nonwoven fabric such that a mask stretched in a vertical direction of a face, and cuts were made on places corresponding to eyes, a mouth and a nose so as to form a shape shown in FIG. 1 to prepare cosmetic facial masks in Example 1 and Comparative Examples 1 to 2.

In Example 1, nonwoven fabric 1 was used, and in Comparative Examples 1 and 2, nonwoven fabrics 2 and 3 were used, respectively.

Cosmetic Liquid Impregnation Method 1

Each cosmetic facial mask in Example 1 and Comparative Examples 1 to 2 was folded once on a longitudinal line passing through the center of the face, subsequently folded once on a transverse line passing through the center thereof, and further folded once on a longitudinal line passing through the center thereof, thus being folded into one eight. Each folded mask was respectively inserted into a zippered polyethylene bag (trade name: Unipack E-4, made by Seisan Nippon Co., Ltd.). Then, as a cosmetic liquid, 18 mL of "ELIXIR SUPERIER Lift Moist Lotion III" (trade name) made by Shiseido Co., Ltd. was injected thereinto, the bag was zipped so as to prevent entry of air. The resulting polyethylene bag in which the mask and the cosmetic liquid were entered was placed on a desk, pressed 10 times by a palm, and then allowed to stand for 1 hour at room temperature. After 1 hour, the mask was removed from the polyethylene bag, and an impregnation condition of the cosmetic liquid was visually confirmed. As a result, the cosmetic liquid was sufficiently impregnated into all masks.

Mask Wearing Test 1

Figure 2:
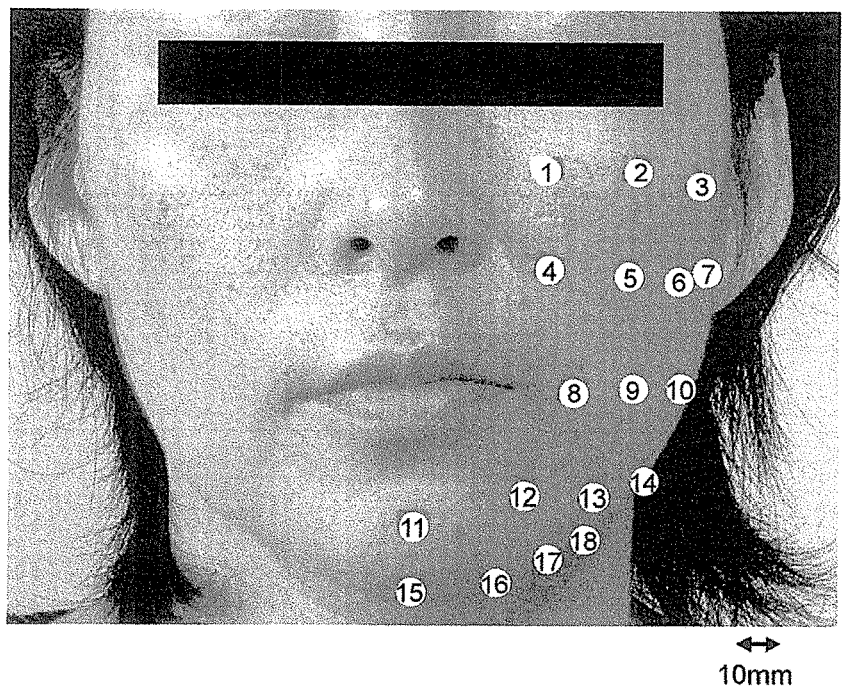
FIG. 2 shows a photograph of a front face of a subject.
Figure 3:
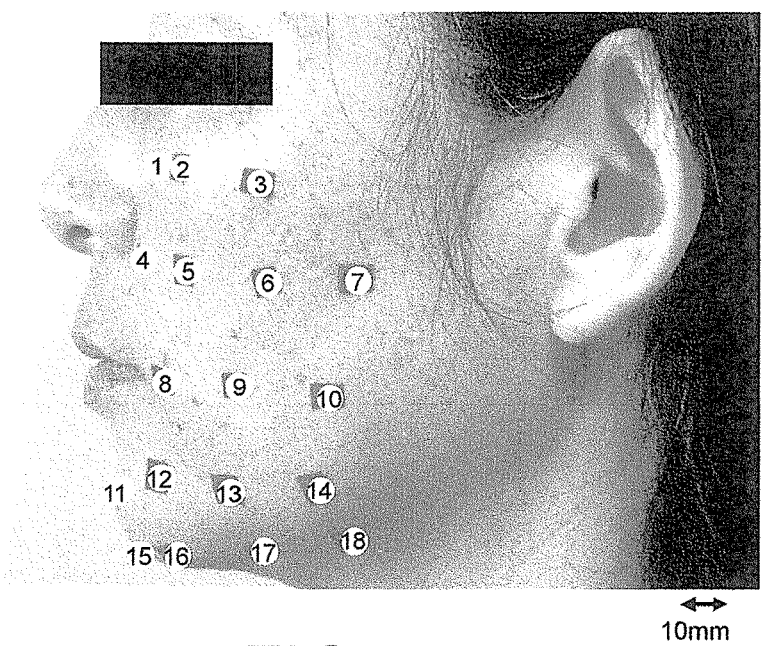
FIG. 3 shows a photograph of a side face of a subject.
Figure 5:
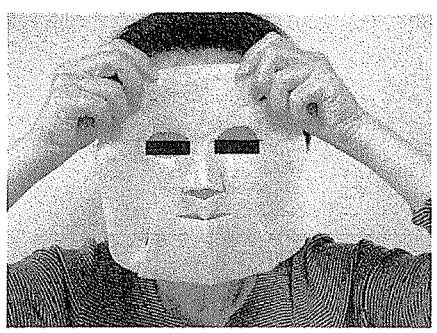
FIG. 5 shows a photograph showing a procedure in one example of a fixing method for a cosmetic facial mask of the invention.

A label was attached on the eye part, the cheek part, the mouth part and the jaw part of a subject (47 years old, woman) using a pressure-sensitive adhesive tape to take photographs of a front face and a side face (FIGS. 2 to 3). Next, in accordance with the cosmetic liquid impregnation method 1, the cosmetic facial mask (Example 1) into which the cosmetic liquid was impregnated was prepared, and a wearing test was conducted to the subject (FIG. 5).

Figure 4:
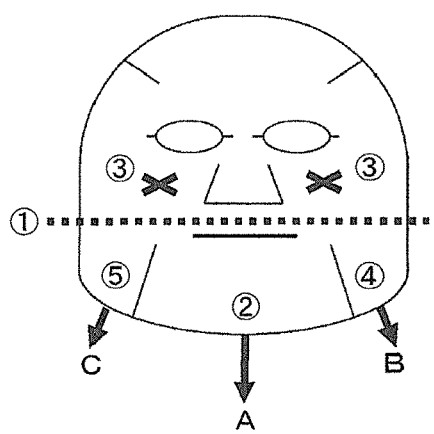
FIG. 4 is a schematic constitutional diagram showing a cosmetic facial mask according to one embodiment of the invention.
Figure 6:
FIG. 6 shows a photograph showing a procedure in one example of a fixing method for a cosmetic facial mask of the invention.

In addition, when the cosmetic facial mask was a laminate as in Example 1, the mask was placed on the face such that an elastomer layer side came in contact with skin to meet positions of the eyes and the nose to be fitted thereon (FIG. 6), and then while a part of the cosmetic facial mask corresponding to the line ① in FIG. 4 was held by the

TABLE 1

Figure 7:
FIG. 7 shows a photograph showing a procedure in one example of a fixing method for a cosmetic facial mask of the invention.
Figure 8:
FIG. 8 shows a photograph showing a procedure in one example of a fixing method for a cosmetic facial mask of the invention.
Figure 9:
FIG. 9 shows a photograph showing a procedure in one example of a fixing method for a cosmetic facial mask of the invention.

| | Material | | Basis weight (gsm) | Physical properties in wet state | | |
|---|---|---|---|---|---|---|
| | Non-elastomeric fiber layer | Elastomer layer | | Stress at 50% elongation (N/25 mm) | Elongation recovery ratio at 50% elongation (%) | Stress at 25% elongation recovery ratio (N/25 mm) |
| Nonwoven fabric 1 (laminate) | Cellulose (60%) Polyester (40%) | Ethylene-octene-1 copolymer (100%) | 58 | 1.5 | 74 | 0.2 |
| Nonwoven fabric 2 | Cellulose (40%) Polyester (37.5%) Low density polyethylene (22.5%) | None | 50 | 1.2 | 22 | 0 |
| Nonwoven fabric 3 | Cellulose (100%) | None | 60 | 22 | 30 | 0 | thumb and the index finger of the right hand or the left hand such that a lower part of nose to a cheek part served as a supporting point, the part ② in FIG. 4 was gripped using another hand, and stretched in the A direction to be fitted and fixed to a lower part of jaw (FIG. 7). Subsequently, while each position ③ in FIG. 4 was held by the thumb and the index finger of the right hand or the left hand, and right-left flap parts ④ and ⑤ in FIG. 4 were stretched in the B or C direction (FIG. 8) to fit and fix the mask from the nose to a lower surface as a whole onto the lower part of jaw (FIG. 9). After 5 minutes from wearing the mask, photographs were taken for a front face and a side face of the subject. Moreover, also for cosmetic facial masks in Comparative Examples 1 to 2, photography was performed after the cosmetic facial masks were worn in identical procedures.

Criteria on Lift-Up Effect

A photograph before wearing a cosmetic facial mask was compared with a photograph during wearing thereof to analyze a change of positions of labels given to the face of a subject. In the analysis, evaluation was made based on criteria on a lift-up effect as described below.

As the criteria on the lift-up effect, a case where the photograph during wearing the cosmetic facial mask met all conditions (1) to (4) described below was rated to be "very effective," a case where the mask met three conditions was rated to be "effective," a case where the mask met two conditions was rated to be "somewhat effective," and a case where the mask met one condition or less was rated to be "non-effective."

(1) In a photograph of the front face, a label position in the jaw part during wearing the mask moved by 3 mm or more toward an ear in a diagonally upper direction or upward direction in comparison with the position before wearing the mask.

(2) In the photograph of the front face, any one of label positions in the mouth part, the cheek part and the eye parts during wearing the mask moved by 3 mm or more toward the ear in a diagonally upper direction or upward direction in comparison with the position before wearing the mask.

(3) In a photograph of a side face, a label position in the jaw part during wearing the mask moved by 3 mm or more toward an ear in a diagonally upper direction or upward direction in comparison with the position before wearing the mask.

(4) In the photograph of the side face, any one of label positions in the mouth part, the cheek part and the eye part during wearing the mask moved by 3 mm or more toward the ear in a diagonally upper direction or upward direction in comparison with the position before wearing the mask.

In accordance with the criteria, the lift-up effect of each cosmetic facial mask was judged.

Figure 10:
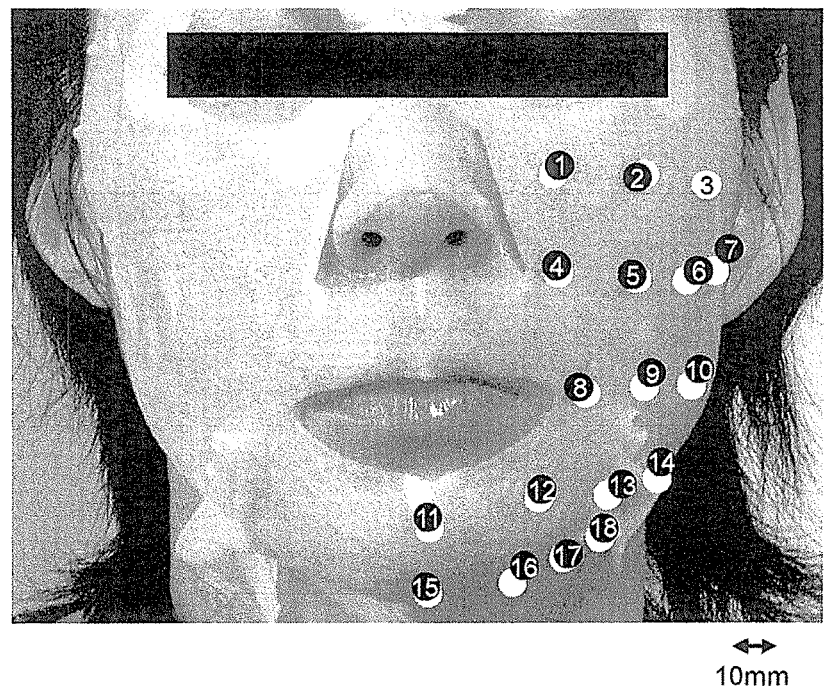
FIG. 10 shows a photograph of a front face, showing a result of Example 1 in which one example of a fixing method for a cosmetic facial mask of the invention is executed.
Figure 11:
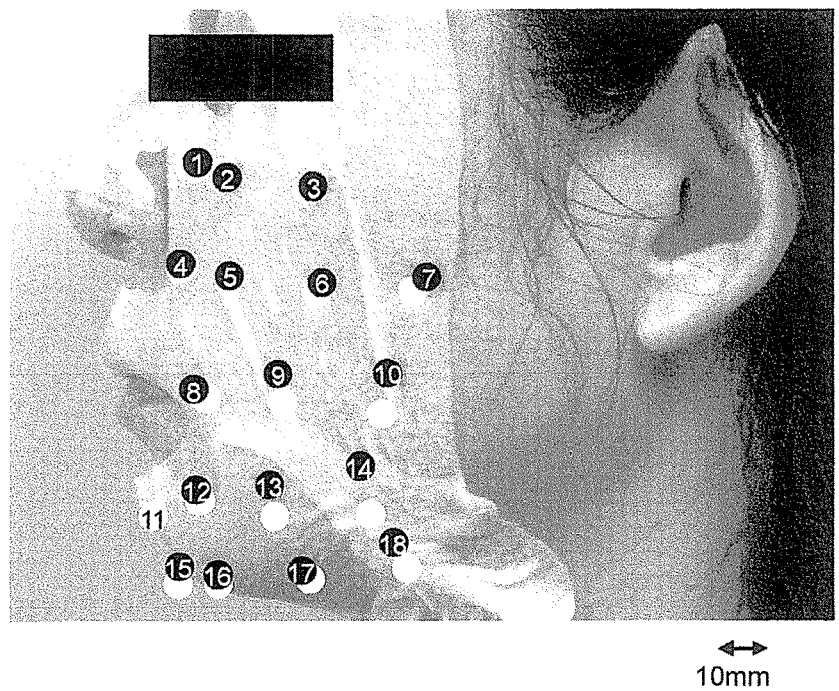
FIG. 11 shows a photograph of a side face, showing a result of Example 1 in which one example of a fixing method for a cosmetic facial mask of the invention is executed.
Figure 12:
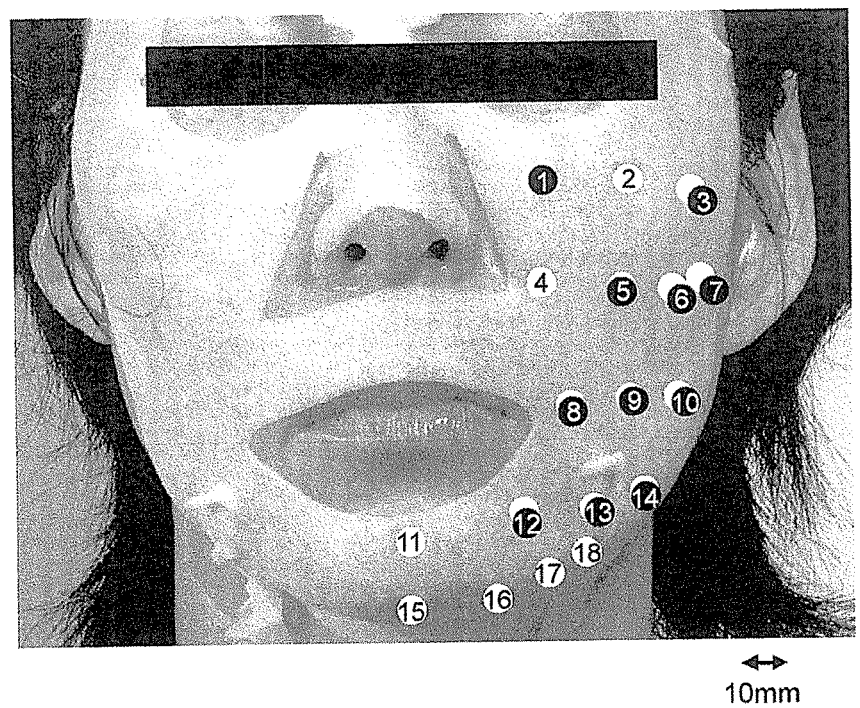
FIG. 12 shows a photograph of a front face, showing a result of Comparative Example 1 in which one example of a fixing method for a cosmetic facial mask of the invention is executed.
Figure 13:
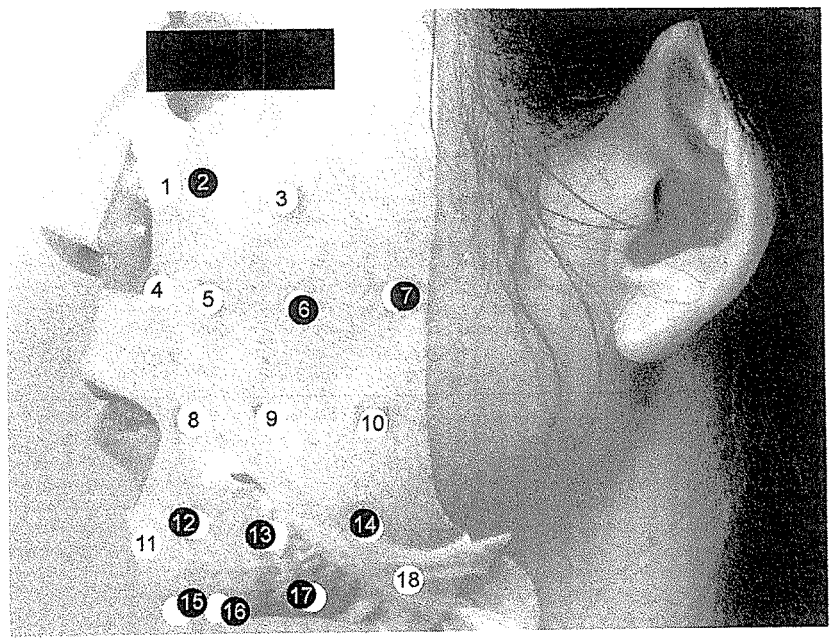
FIG. 13 shows a photograph of a side face, showing a result of Comparative Example 1 in which one example of a fixing method for a cosmetic facial mask of the invention is executed.
Figure 14:
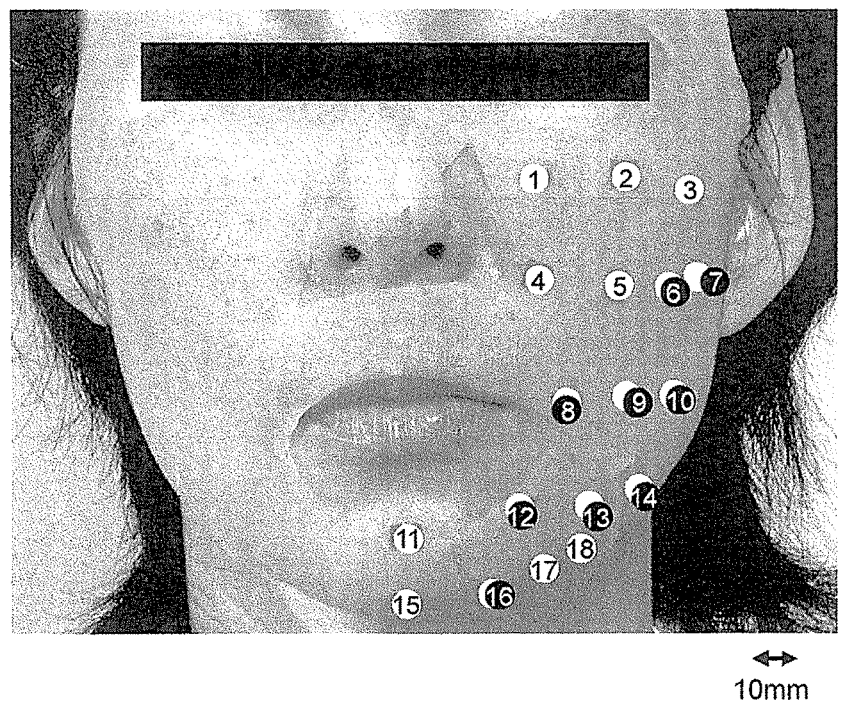
FIG. 14 shows a photograph of a front face, showing a result of Comparative Example 2 in which one example of a fixing method for a cosmetic facial mask of the invention is executed.
Figure 15:
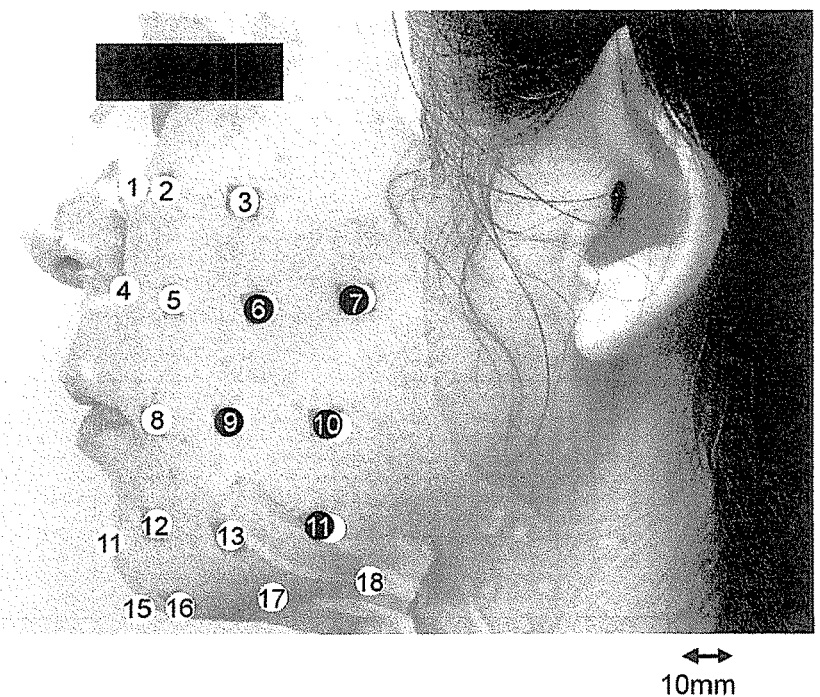
FIG. 15 shows a photograph of a side face, showing a result of Comparative Example 2 in which one example of a fixing method for a cosmetic facial mask of the invention is executed.

For each of photographs in Example 1 (FIGS. 10 to 11), in Comparative Example 1 (FIGS. 12 to 13) and in Comparative Example 2 (FIGS. 14 to 15), a label position before wearing the mask was plotted using a white circle (○), and a label position a movement of which was recognized during wearing the mask was plotted using a black circle (●), and comparison was made. As a result, the mask in Example 1 met all of the conditions (1) to (4), and therefore judged to be "very effective." Moreover, the maximum movement distance of the label was 9 mm in the jaw part/vertical direction (site (14) in FIG. 11), 6 mm in the mouth part/vertical direction (site (9) in FIG. 11) and 4 mm in the cheek part/vertical direction (sites (6), (7) in FIG. 11), and an excellent lift-up effect was demonstrated in all sites of the jaw part, the mouth part and the cheek part. In contrast, the cosmetic facial masks in Comparative Examples 1 and 2 met none of the conditions (1) to (4), and therefore was judged to be "non-effective."

Further, the subject was interviewed with regard to a use feeling for each mask. Table 2 shows the results. As a result of interview, the cosmetic facial mask in Example 1 was evaluated to be satisfactory in all of ease of handling, a wearing feeling, a fitting feeling, a tightening feeling, a lift-up feeling and difficulty in dripping. Moreover, a remark was expressed in which the lift-up feeling was sensed in the jaw part as a whole.

In contrast, the mask in Comparative Example 1 was evaluated to give no sense of the tightening feeling and the lift-up feeling at all, while the ease of wearing, the wearing feeling, the fitting feeling and difficulty in dripping were evaluated to be satisfactory. Moreover, the mask in Comparative Example 2 was evaluated to give no sense of the tightening feeling and the lift-up feeling, and also to be hard to handle due to excessively high draping properties, while the wearing feeling, the fitting feeling and difficulty in dripping were evaluated to be satisfactory.

TABLE 2

| | Ease of handling | Wearing feeling | Fitting feeling | Tightening feeling | Lift-up feeling | Difficulty in dripping |
| --- | --- | --- | --- | --- | --- | --- |
| Example 1 | Excellent | Excellent | Excellent | Excellent | Excellent | Excellent |
| Comparative Example 1 | Excellent | Excellent | Excellent | Bad | Bad | Excellent |
| Comparative Example 2 | Bad | Excellent | Excellent | Bad | Bad | Excellent |

Excellent > Somewhat good > Marginal > Bad

Preparation 2 of Cosmetic Facial Mask (Example 2, Comparative Examples 3 to 4)

Figure 16:
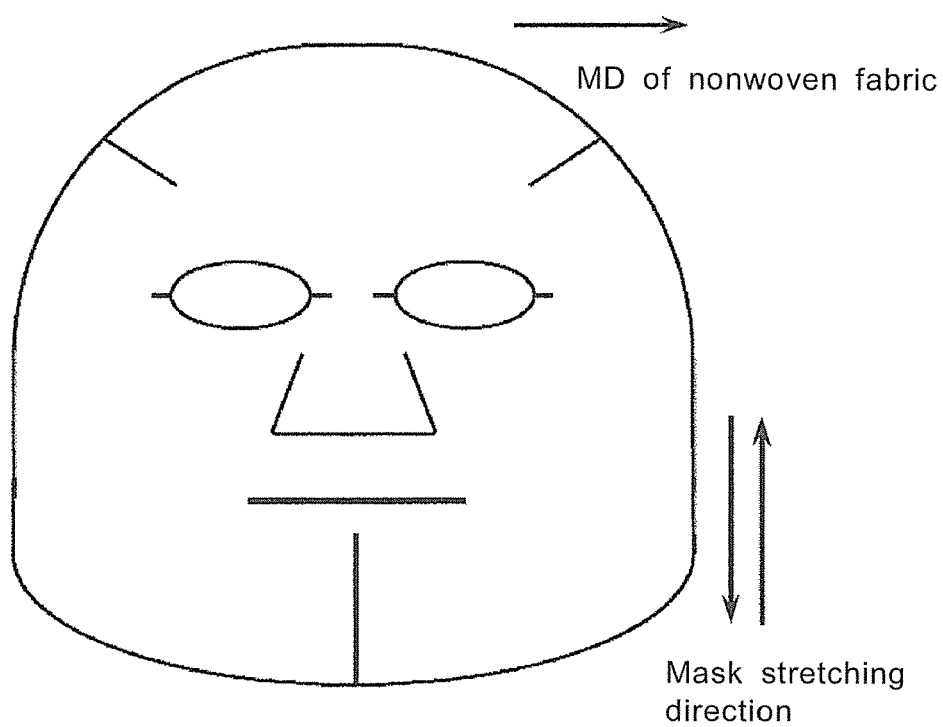
FIG. 16 is a schematic constitutional diagram showing a cosmetic facial mask according to one embodiment of the invention.

A cosmetic facial mask was obtained in accordance with Example 1 and Comparative Examples 1 to 2 except that the cosmetic facial mask was processed into a shape shown in FIG. 16.

Cosmetic Liquid Impregnation Method 2

A cosmetic liquid was impregnated into each mask in accordance with the cosmetic liquid impregnation method 1. When the mask was removed by opening the zipper of the polyethylene bag after 1 hour, the impregnation condition of the cosmetic liquid was visually confirmed. The cosmetic liquid was confirmed to be sufficiently impregnated into all masks.

Mask Wearing Test 2

Figure 17:
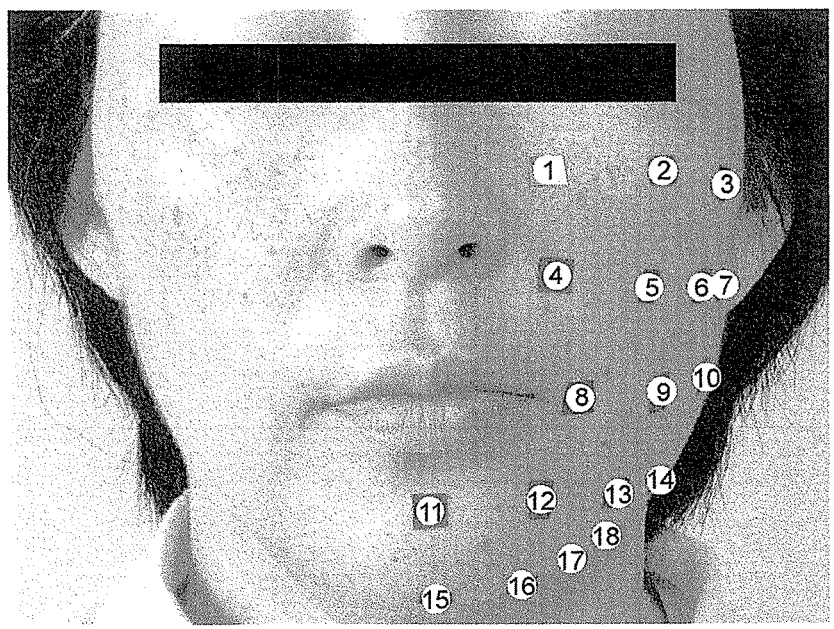
FIG. 17 shows a photograph of a front face of a subject.
Figure 18:
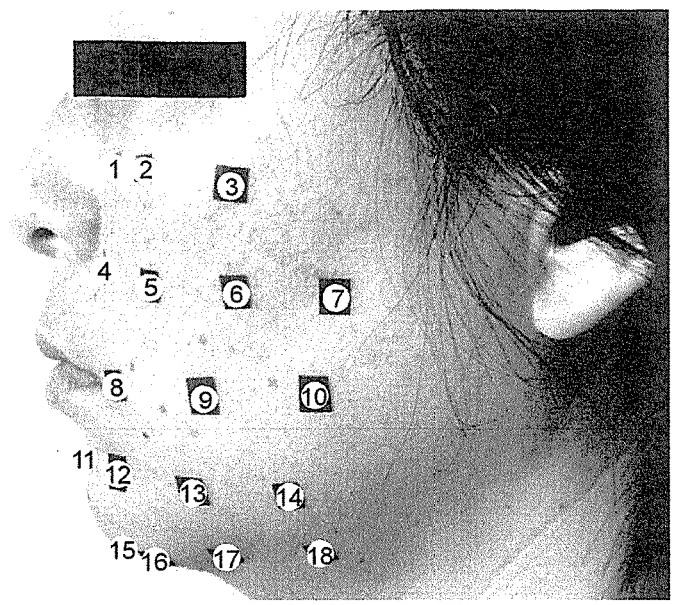
FIG. 18 shows a photograph of a side face of a subject.

The eye part, the cheek part, the mouth part and the jaw part of a subject (47 years old, woman) were labeled using a polyvinyl chloride tape ("Eslon tape #360, made by Sekisui Chemical Co., Ltd.), and then photographs of the front face and the side face were taken (FIGS. 17 to 18).

Figure 19:
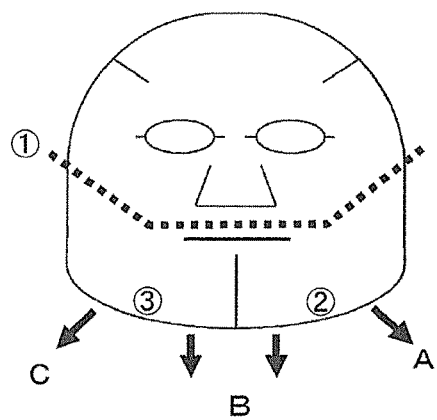
FIG. 19 is a schematic constitutional diagram showing a cosmetic facial mask according to one embodiment of the invention.
Figure 20:
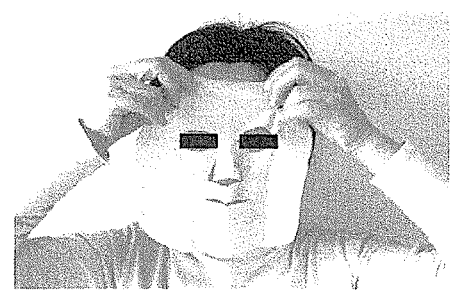
FIG. 20 shows a photograph showing a procedure in one example of a fixing method for a cosmetic facial mask of the invention.
Figure 21:
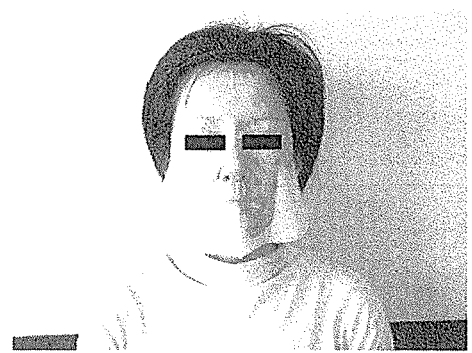
FIG. 21 shows a photograph showing a procedure in one example of a fixing method for a cosmetic facial mask of the invention.
Figure 22:
FIG. 22 shows a photograph showing a procedure in one example of a fixing method for a cosmetic facial mask of the invention.
Figure 23:
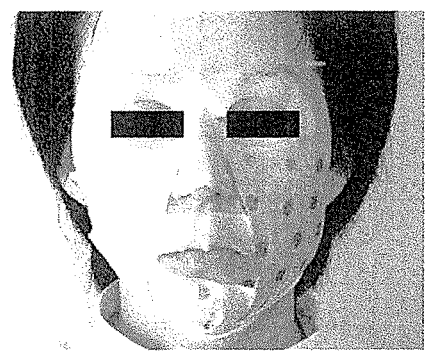
FIG. 23 shows a photograph showing a procedure in one example of a fixing method for a cosmetic facial mask of the invention.

Next, the cosmetic facial mask in Example 2 was removed from the polyethylene bag (FIG. 20). When the cosmetic facial mask was a laminate as in Example 2, the mask was placed on the face such that an elastomer layer side came in contact with skin to meet positions of the eyes and the nose to be fitted thereon (FIG. 21), and then while the line ① in FIG. 19 was held using the thumb and the index finger of the right hand or the left hand such that a lower part of nose to the temple part served as a supporting point, the flap parts ② and ③ in FIG. 19 were gripped using another hand, and stretched in each direction of A, B and C (FIG. 22), and a mask lower surface as a whole was fitted and fixed to a lower part of the jaw (FIG. 23). After 5 minutes from wearing the mask, photographs were taken for the front face and the side face of the subject. Moreover, also for cosmetic facial masks in Comparative Examples 3 to 4, photography was performed after wearing the cosmetic facial mask in identical procedures.

Figure 24:
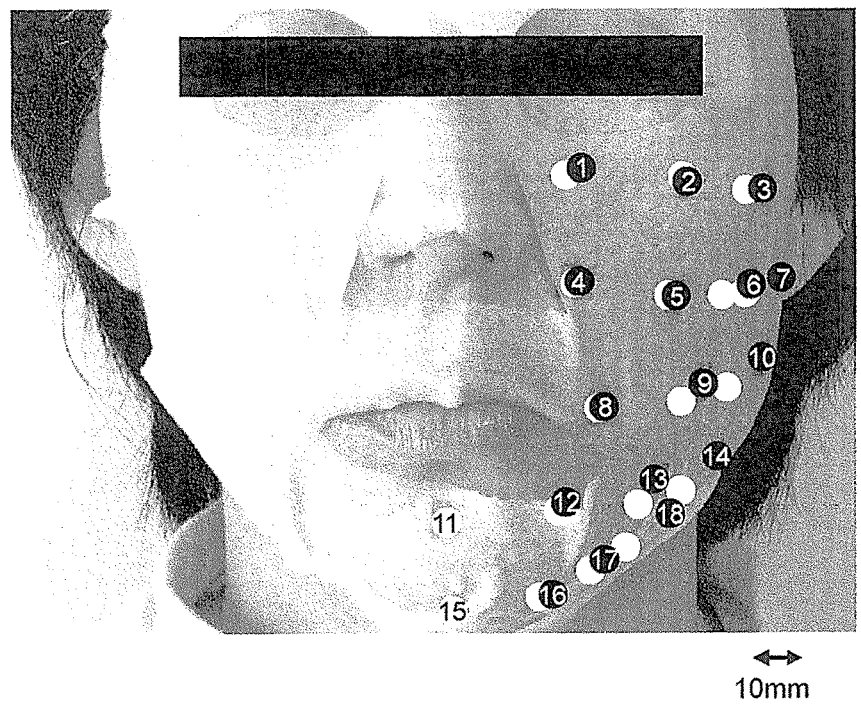
FIG. 24 shows a photograph of a front face, showing a result of Example 2 in which one example of a fixing method for a cosmetic facial mask is executed.
Figure 26:
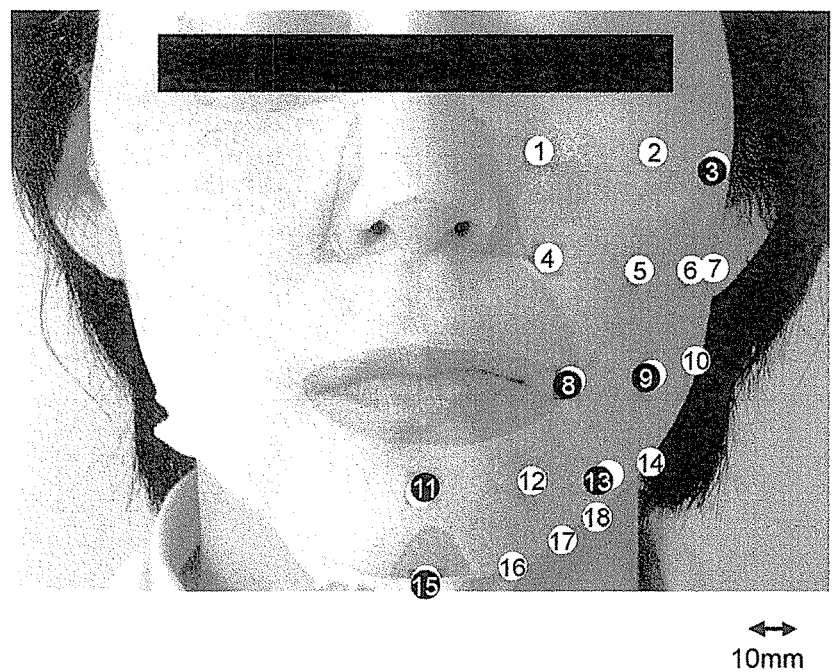
FIG. 26 shows a photograph of a front face, showing a result of Comparative Example 3 in which one example of a fixing method for a cosmetic facial mask is executed.
Figure 27:
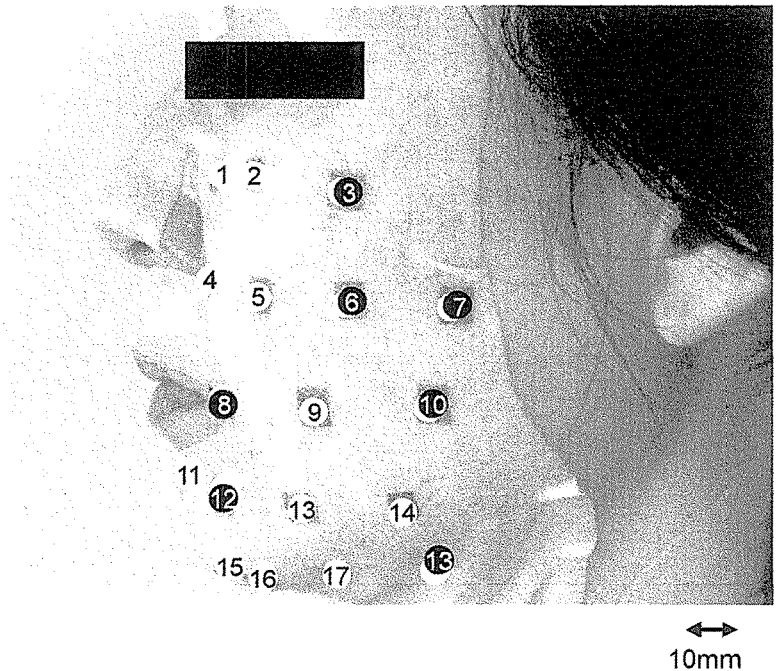
FIG. 27 shows a photograph of a side face, showing a result of Comparative Example 3 in which one example of a fixing method for a cosmetic facial mask is executed.
Figure 28:
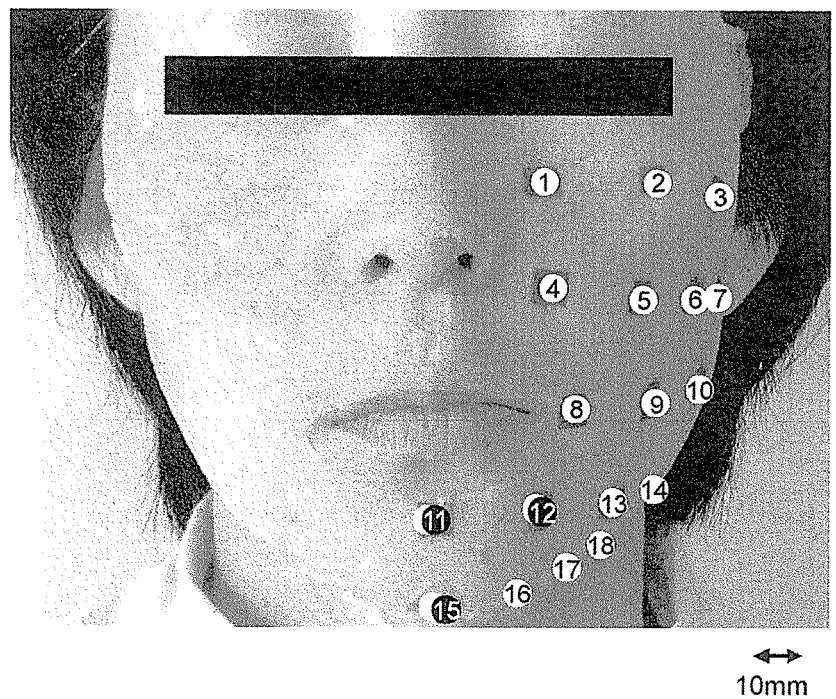
FIG. 28 shows a photograph of a front face, showing a result of Comparative Example 4 in which one example of a fixing method for a cosmetic facial mask is executed.
Figure 29:
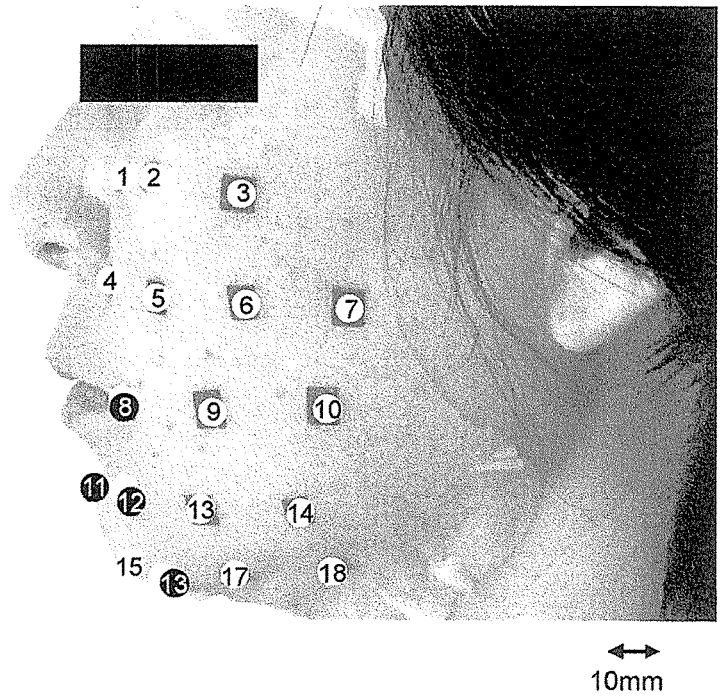
FIG. 29 shows a photograph of a side face, showing a result of Comparative Example 4 in which one example of a fixing method for a cosmetic facial mask is executed.

In accordance with the Criteria on lift-up effect described above, the effect that the cosmetic facial masks in Example 2 and Comparative Examples 3 to 4 gave a lift-up feeling was judged. For each photograph in Example 2 (FIGS. 24 to 25), Comparative Example 3 (FIGS. 26 to 27) and Comparative Example 4 (FIGS. 28 to 29), a label position before wearing the mask was plotted using a white circle and a label position a movement of which was recognized during wearing the mask was plotted using a black circle, and comparison was made.

Figure 25:
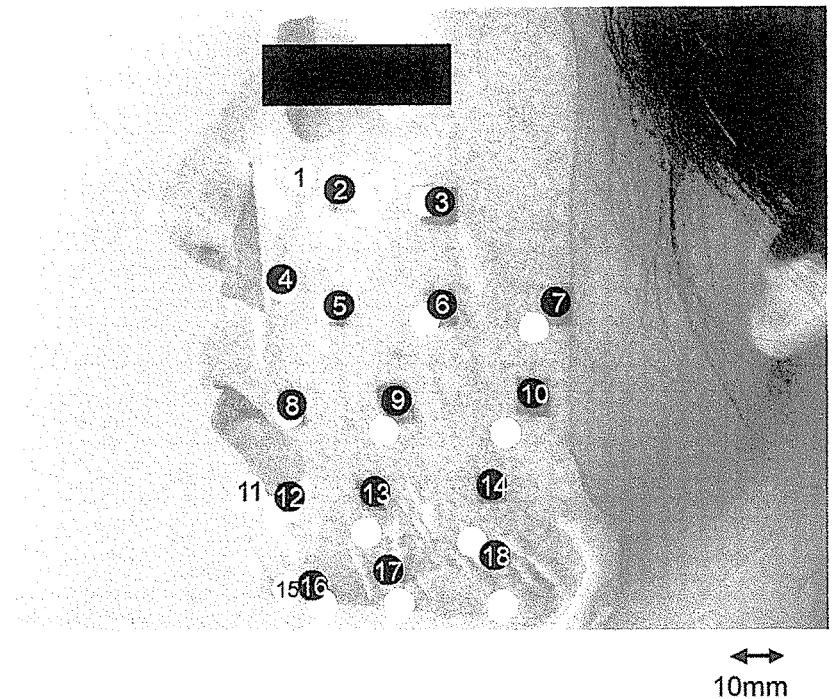
FIG. 25 shows a photograph of a side face, showing a result of Example 2 in which one example of a fixing method for a cosmetic facial mask is executed.

As a result, the mask in Example 2 met all of the conditions (1) to (4), and therefore judged to be "very effective." Moreover, a maximum movement distance of the label was 11 mm in the jaw part/vertical direction, (site (14) in FIG. 25), 8 mm in the mouth part/vertical direction (site (9) in FIG. 25) and 8 mm in the cheek part/vertical direction (site (10) in FIG. 25), and an excellent lift-up effect was demonstrated in all sites of the jaw part, the mouth part and the cheek part. In contrast, the cosmetic facial mask in Comparative Example 3 met only condition (1), and therefore was judged to be "non-effective." Moreover, the mask in Comparative Example 4 met none of the conditions (1) to (4), and therefore was judged to be "non-effective."

Further, the subject was interviewed with regard to the use feeling for each mask. Table 3 shows the results. As a result of interview, the cosmetic facial mask in Example 2 was evaluated to be satisfactory in all of ease of handling, the wearing feeling, the fitting feeling, the tightening feeling, the lift-up feeling and difficulty in dripping. Moreover, evaluation was made in which the lift-up feeling was sensed in the jaw part in comparison with the mask in Example 1. In contrast, the mask in Comparative Example 3 was evaluated to give no sense of the tightening feeling and the lift-up feeling at all, while the ease of wearing, the wearing feeling, the fitting feeling and difficulty in dripping were evaluated to be satisfactory. Moreover, the mask in Comparative Example 4 was evaluated to give no sense of the tightening feeling and the lift-up feeling at all, and also to be hard to handle due to excessively high draping properties, while the wearing feeling, the fitting feeling and difficulty in dripping were evaluated to be satisfactory.

TABLE 3

| | Ease of handling | Wearing feeling | Fitting feeling | Tightening feeling | Lift-up feeling | Difficulty in dripping |
|---|---|---|---|---|---|---|
| Example 2 | Excellent | Excellent | Excellent | Excellent | Excellent | Excellent |
| Comparative Example 3 | Excellent | Excellent | Excellent | Bad | Bad | Excellent |
| Comparative Example 4 | Bad | Excellent | Excellent | Bad | Bad | Excellent |

Excellent > Somewhat good > Marginal > Bad

Preparation 3 of Cosmetic Facial Mask
(Example 3)

Figure 30:
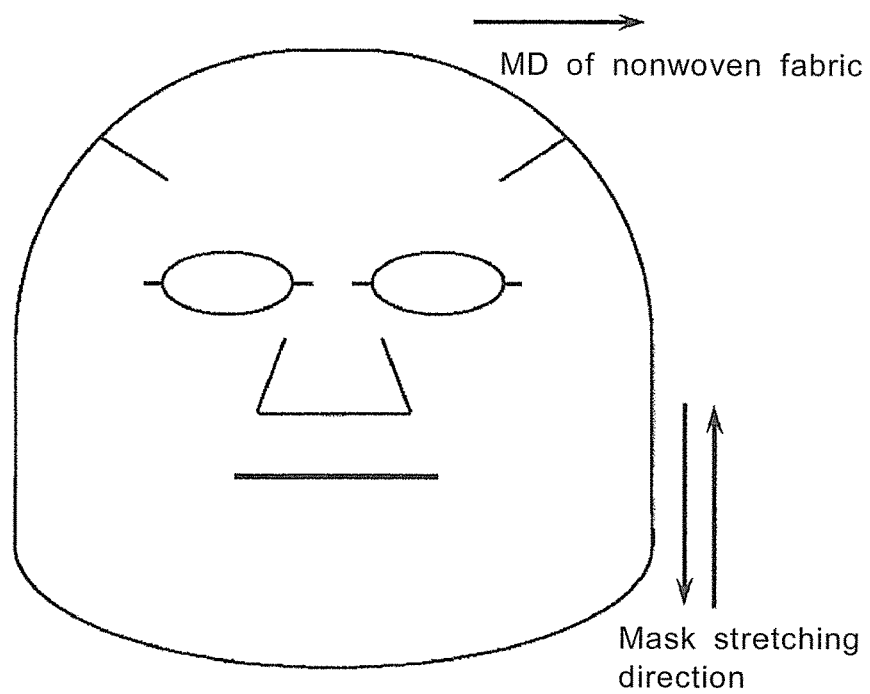
FIG. 30 is a schematic constitutional diagram showing a cosmetic facial mask according to one embodiment of the invention.

A cosmetic facial mask was obtained in accordance with Example 1 except that it had been processed into a shape shown in FIG. 30.

Cosmetic Liquid Impregnation Method 3

A cosmetic liquid was impregnated into each mask in accordance with the cosmetic liquid impregnation method 1. When the mask was removed by opening the zipper of the polyethylene bag after 1 hour, the impregnation condition of the cosmetic liquid was visually confirmed. The cosmetic liquid was confirmed to be sufficiently impregnated into all masks.

Mask Wearing Test 3

Figure 31:
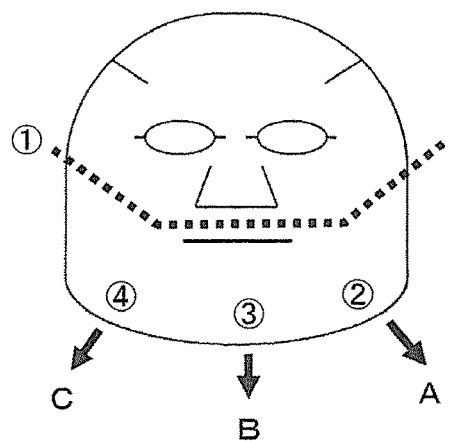
FIG. 31 is a schematic constitutional diagram showing a cosmetic facial mask according to one embodiment of the invention.

A mask wearing test was conducted in a manner similar to the mask wearing test 2 except that, while the line ① in FIG. 31 was held using the thumb and the index finger of the right hand or the left hand such that a lower part of nose to the temple part served as a supporting point, the parts ②, ③ and ④ in FIG. 31 were gripped using another hand, and stretched in each direction of A, B and C, and a mask lower surface as a whole was fitted and fixed to a lower part of the jaw.

Figure 32:
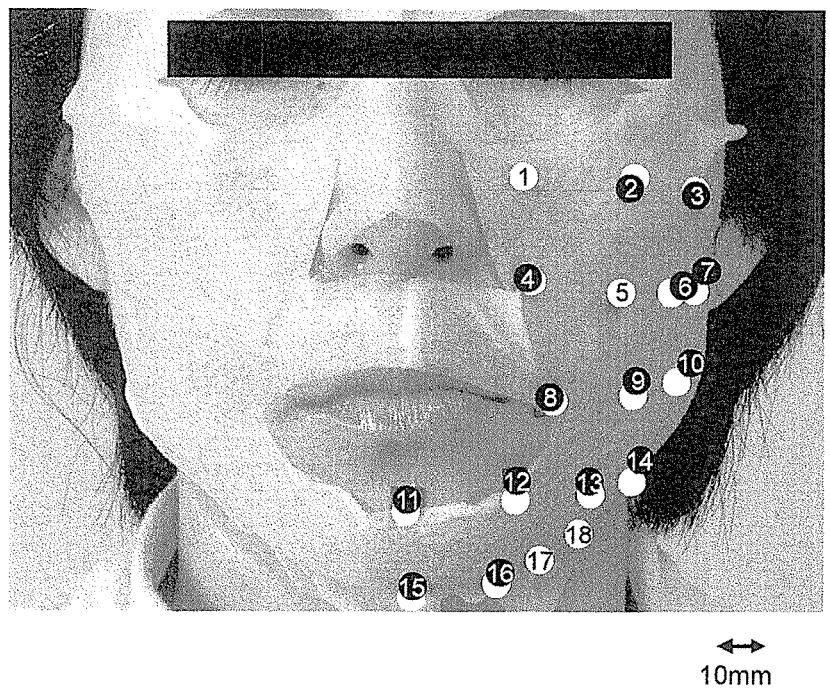
FIG. 32 shows a photograph of a front face, showing a result of Example 3 in which one example of a fixing method for a cosmetic facial mask of the invention is executed.
Figure 33:
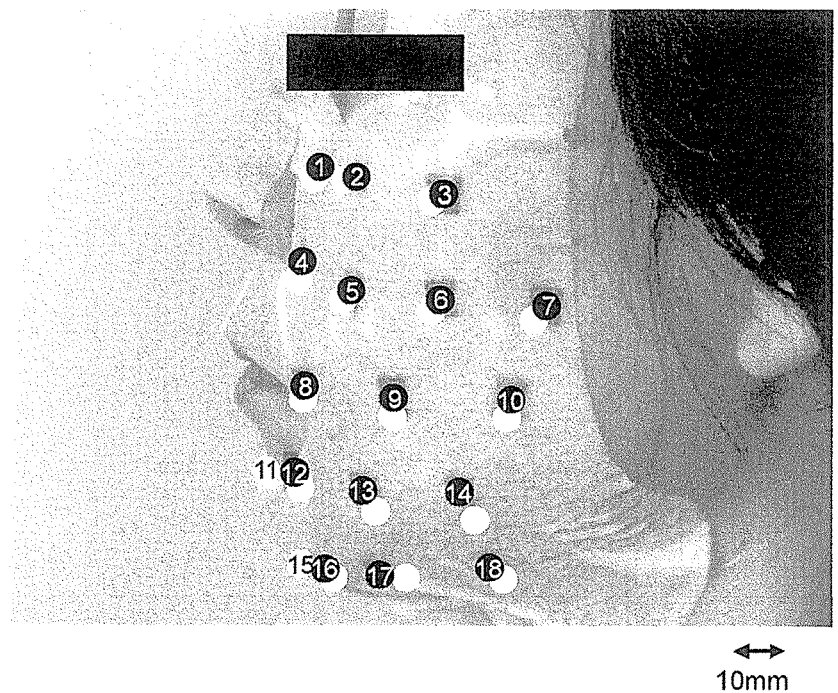
FIG. 33 shows a photograph of a side face, showing a result of Example 3 in which one example of a fixing method for a cosmetic facial mask of the invention is executed.

In accordance with the Criteria on lift-up effect described above, a lift-up effect of the cosmetic facial mask in Example 3 was judged. For photographs in FIGS. 32 to 33, a label position before wearing the mask was plotted using a white circle and a label position a movement of which was recognized during wearing the mask was plotted using a black circle, and comparison was made. As a result, the mask in Example 3 met all of the conditions (1) to (4), and therefore judged to be "very effective." Moreover, a maximum movement distance of the label was 8 mm in the jaw part/vertical direction, (site (14) in FIG. 33), 6 mm in the mouth part/vertical direction (site (9) in FIG. 33), and 5 mm in the cheek part/vertical direction (site (10) in FIG. 33), and an excellent lift-up effect was demonstrated in all sites of the jaw part, the mouth part and the cheek part.

Further, the subject was interviewed with regard to a use feeling for the mask in Example 3. Table 4 shows the results. As a result of interview, the cosmetic facial mask in Example 3 was evaluated to be satisfactory in all of ease of handling, the wearing feeling, the fitting feeling, the tightening feeling, the lift-up feeling and difficulty in dripping. Moreover, in comparison with the masks in Examples 1 and 2, the mask in Example 3 was evaluated to give a sense of a further uniform tightening feeling in the lower part of face as a whole, while the lift-up feeling of the jaw part was evaluated to be poorer.

TABLE 4

| | Ease of handling | Wearing feeling | Fitting feeling | Tightening feeling | Lift-up feeling | Difficulty in dripping |
|---|---|---|---|---|---|---|
| Example 3 | Excellent | Excellent | Excellent | Excellent | Excellent | Excellent |

Excellent > Somewhat good > Marginal > Bad

INDUSTRIAL APPLICABILITY

The cosmetic facial mask of the invention has moderate stretchability and stress at elongation in a vertical direction of the face, and therefore is suitable for a use method for achieving lift-up of a flaccid cheek or face line, and a beauty regimen adopting the use method. Specifically, the mask can be suitably used for a cosmetic facial mask used in household, and a cosmetic facial mask used in an aesthetic salon or the like.

The invention claimed is:

1. A cosmetic facial mask, comprising:
   a first member constituted to cover a part of a face, comprising a laminate in which a non-elastomeric fiber layer and an elastomer layer are integrated through lamination, and having stretchability in a vertical direction of the cosmetic facial mask; and
   a second member constituted to cover another part of the face, having stretchability in a direction other than the vertical direction of the cosmetic facial mask, or having no stretchability,
   wherein the cosmetic facial mask has two first openings at positions corresponding to eyes of a user and one second opening at a position corresponding to a nose of the user, and the vertical direction of the cosmetic facial mask is defined by the position of the second opening and a middle position of the positions of the two first opening.

2. The cosmetic facial mask according to claim 1, wherein a stress of the first member at 50% elongation in a wet state is in a range of 0.4 to 5.0 N/25 mm, and an elongation recovery ratio of the first member at 50% elongation in the wet state is 50% or more.

3. The cosmetic facial mask according to claim 1, wherein a stress of the first member at 25% elongation recovery in a wet state is in a range of 0.02 to 1.5 N/25 mm.

4. The cosmetic facial mask according to claim 1, wherein the non-elastomeric fiber layer is subjected to nonwoven fabric formation by entangling fibers with each other in a fiber layer in a thickness direction of the fiber layer.

5. The cosmetic facial mask according to claim 1, wherein the elastomer layer comprises a nonwoven fabric formed by at least one kind of method selected from the group of a melt-blown method and a spunbond method.

6. A method for using a cosmetic facial mask, comprising: providing the cosmetic facial mask as recited in claim 1, wherein the first member of the cosmetic facial mask is worn while being stretched in a downward direction and/or a right-left diagonally downward direction of a face by applying an arbitrary one or more points of a temple part, a cheek part and a lower part of a nose as a supporting point.

7. A beautifying method, comprising:
   providing the cosmetic facial mask as recited in claim 1;
   wearing the cosmetic facial mask; and
   keeping the cosmetic facial mask on the face.

8. The cosmetic facial mask according to claim 1, wherein the non-elastomeric fiber layer includes a fiber layer obtained by aligning fibers by carding, and an alignment direction of the fibers coincides with a cross direction of the cosmetic facial mask that is perpendicular to the vertical direction of the cosmetic facial mask, so that the cosmetic facial mask has stretchability in the vertical direction of the cosmetic facial mask.

* * * * *